(12) United States Patent
Fujii et al.

(10) Patent No.: US 6,656,111 B2
(45) Date of Patent: Dec. 2, 2003

(54) CONTROL DEVICE FOR AN ENDOSCOPE

(75) Inventors: Yoshinori Fujii, Saitama (JP); Akira Sugiyama, Kanagawa (JP); Hiroyuki Katsurada, Tokyo (JP)

(73) Assignee: Pentax Corporation, Tokyo (JP)

( * ) Notice: Subject to any disclaimer, the term of this patent is extended or adjusted under 35 U.S.C. 154(b) by 245 days.

(21) Appl. No.: 09/836,221

(22) Filed: Apr. 18, 2001

(65) Prior Publication Data

US 2001/0034472 A1 Oct. 25, 2001

(30) Foreign Application Priority Data

Apr. 19, 2000 (JP) ............................... 2000-117681
Jun. 22, 2000 (JP) ............................... 2000-187801
Aug. 25, 2000 (JP) ............................... 2000-256075

(51) Int. Cl.[7] ................................................. A61B 1/00
(52) U.S. Cl. ................................... 600/146; 600/139
(58) Field of Search .............................. 600/146, 139, 600/152, 122

(56) References Cited

U.S. PATENT DOCUMENTS 5,924,977 A * 7/1999 Yabe et al. ................. 600/121

* cited by examiner

Primary Examiner—Thor Campbell
(74) Attorney, Agent, or Firm—Greenblum & Bernstein, P.L.C.

(57) ABSTRACT

An endoscope includes a hollow operational body, a hollow shaft provided on the hollow operational body, at least one hollow rotational control knob which is rotatably supported on the hollow shaft; and an air passage via which an inner space of the hollow operational body and an inner space of the at hollow rotational control knob have a communicative connection with each other, wherein the hollow shaft includes a portion of the passage.

26 Claims, 25 Drawing Sheets

CONTROL DEVICE FOR AN ENDOSCOPE

BACKGROUND OF THE INVENTION

1. Field of the Invention

The present invention relates to a control device having a steering device for steering the bendable distal end of an endoscope.

2. Description of the Related Art

Endoscopes provided with a pair of angle knobs for steering the distal end of the insertion portion of the endoscope, and a corresponding pair of lock knobs which respectively lock the pair of angle knobs to thereby lock the distal end of the insertion portion are known in the art. Among such endoscopes, endoscopes whose angle knobs and/or lock knobs are formed as hollow knobs are also known in the art.

Medical endoscopes need to be disinfected and sterilized each time before use. In the case of sterilizing a medical endoscope with gas, the endoscope is sterilized through the use of difference in pressure between the internal and external pressures of the endoscope. Therefore, the stress due to pressure fluctuation tends to be applied to elements of the hollow angle knobs and/or lock knobs since the volume of the inner space of each angle or lock knob is generally small. In medical endoscopes which are intended to be sterilized with gas, in order to make the endoscopes compliant with such stress, the wall thickness of each hollow knob is made heavy while the adhesive coated surface of the same is made large, if any hollow knob has such a surface, to retain a sufficient strength of each hollow knob. However, from a view point of minimization, reduction in weight, and productivity of the endoscope, both the wall thickness and the adhesive coated surface are preferably small.

In conventional endoscopes, in the case where a hollow angle knob is formed as a hollow member which includes upper and lower walls which are separate from each other in the direction of the axis of the central rotational shaft, and an outer peripheral wall which connects the upper and lower walls in assembled condition, such a hollow angle knob generally has a two-piece construction. Namely, such a hollow angle knob includes a first half piece including the upper wall and an upper half of the outer peripheral wall and a second half piece including the lower wall and a lower half of the outer peripheral wall, wherein the first half piece and the second half piece are coupled to each other to form the hollow angle knob. According to this conventional structure, since the hollow angle knob is constructed from two or more external elements, it is troublesome and time-consuming to make the two or more external elements independent of each other, while the two or more external elements have to be assembled while ensuring the watertight construction of the hollow angle knob. As a result, the hollow angle knob cannot be made easily at a low cost of production. Furthermore, in the above described case where the hollow angle knob is constructed from the first half piece and the second half piece, a mold seam is inevitably formed on the outer peripheral wall of the hollow angle knob. Such a mold seam makes it difficult and time-consuming to wash and clean the angle knob after the endoscope is used.

A conventional medical endoscope is generally provided with a operational body having a grip portion, and an insertion portion which extends from the operational body. In the case where the insertion portion is a flexible insertion tube, the distal end of the insertion portion serves as a steerable bendable portion which can be steered to bend right, left, upward and downward by controlling a steering device (an L-R angle knob and a U-D angle knob) provided on the operational body. The operator manually controls the angle knobs while holding the grip portion of the operational body during the use of the endoscope. The grip portion and each angle knob are generally made of a resin. Therefore, the external surfaces of the angle knobs and the grip portion are slippery, which may cause a medical accident. To prevent this problem from occurring, an endoscope whose grip portion has an anti-slip knurled surface is known in the art. However, such a knurled surface is not good enough to prevent such a problem from occurring; furthermore, such a knurled surface makes it difficult to wash and clean the endoscope.

SUMMARY OF THE INVENTION

It is an object of the present invention to provide a control device of an endoscope which is lightweight with an outstanding manufacturability, and which cannot be easily damaged even if a large difference in pressure occurs between the outside and the inside of the endoscope.

It is another object of the present invention to provide a control device of an endoscope which can be produced at a low cost of production and which contributes to the maintainability of the endoscope, e.g., ease of cleaning the endoscope.

It is another object of the present invention to provide a control device of an endoscope whose operational body can be securely held, gripped and controlled with little possibility of the operational body slipping off the hand of the operator, or the fingers of the operator slipping off a rotational control knob during the use of the endoscope.

Other objects of the invention will become apparent to one skilled in the art in the following disclosure and the appended claims.

To achieve the object mentioned above, according to an aspect of the present invention, an endoscope is provided, including a hollow operational body, a hollow shaft provided on the hollow operational body, at least one hollow rotational control knob which is rotatably supported on the hollow shaft, and an air passage via which an inner space of the hollow operational body and an inner space of the at hollow rotational control knob have a communicative connection with each other, wherein the hollow shaft includes a portion of the passage.

In an embodiment, the hollow rotational control knob is positioned about an axis of the hollow shaft at an intermediate position between opposite ends of the axis. The air passage includes at least one radial path formed on the hollow shaft to extend in a radial direction of the hollow shaft to the inner space of the hollow rotational control knob; and at least one axial path formed in the hollow shaft so as to have a communicative connection with the radial path, and to extend in a direction of the axis of the hollow shaft to the inner space of the hollow operational body.

Preferably, the endoscope further includes at least one cylindrical member which is fitted on the hollow shaft, wherein the hollow rotational control knob is positioned about an axis of the hollow shaft at an intermediate position between opposite ends of the axis. The air passage includes at least one axial path formed in the hollow shaft to extend in a direction of the axis of the hollow shaft to the inner space of the hollow operational body; at least one first radial path formed on the hollow shaft to extend in a radial direction of the hollow shaft from the axial path to an outer peripheral surface of the hollow shaft; at least one second radial path formed on the cylinder to extend in the direction of the axis of the hollow shaft so as to provide a communicative connection with the axial path and the inner space of the hollow rotational control via the second radial path regardless of a relative rotational position between the cylindrical member and the hollow shaft.

In an embodiment, the hollow rotational control knob is fixed to the cylindrical member so that the cylindrical member rotates about the hollow shaft together with the hollow rotational control knob when the hollow rotational control knob is turned.

In an embodiment, the at least one hollow rotational control knob includes two hollow rotational control knobs which are positioned about the axis of the hollow shaft at different position between opposite ends of the axis, and the inner space of each of the two hollow rotational control knobs have a communicative connection with the inner space of the hollow operational body via the air passage.

In an embodiment, the endoscope further includes another hollow rotational control knob which is positioned at one end of the hollow shaft to be rotatable about the axis of the hollow shaft. An inner space of this hollow rotational control knob and the inner space of the hollow operational body have a communicative connection with each other via the axial path.

In an embodiment, the endoscope further includes an insertion portion connected to the hollow operational body, wherein the hollow rotational control knob functions as a manually rotatable control member to bend a steerable distal end of the insertion portion so as to direct a tip of the distal end toward a target.

In an embodiment, the endoscope further includes an insertion portion connected to the hollow operational body; and another hollow rotational control knob which is positioned at one end of the hollow shaft to be rotatable about the axis of the hollow shaft. The hollow rotational control knob functions as a manually rotatable control member to bend a steerable distal end of the insertion portion so as to direct a tip of the distal end toward a target; and this hollow rotational control knob functions as a manually rotatable lock member to lock the rotational steering knob.

According to another aspect of the present invention, an endoscope is provided, including a hollow operational body, at least one hollow rotational control knob provided on the hollow operational body, and a communicative connection device which provides a communicative connection with an inner space of the hollow operational body and an inner space of the hollow rotational control knob. The communicative connection device includes a stationary hollow shaft about which the at least one hollow rotational control knob is turned.

Preferably, the at least one hollow rotational control knob includes a first angle knob for bending a distal end of an insertion portion of the endoscope in a first direction, a second angle knob for bending the distal end in a second direction perpendicular to the first direction, and a lock knob, positioned at one end of the hollow shaft, for locking the first knob.

According to another aspect of the present invention, an endoscope is provided, including an insertion portion provided at a distal end thereof with a steerable bendable portion; and at least one rotational steering knob which is controlled manually to bend the steerable bendable portion so as to direct a tip of the steerable bendable portion toward a target. The rotational steering knob is made of a resin material and includes a pair of walls which are separate from each other in a direction of a rotational axis of the rotational steering knob, an aperture being formed on each of the pair of walls, and an outer peripheral wall which extends to connect the pair of walls so as to form the rotational steering knob as a hollow knob.

In an embodiment, the rotational steering knob is formed by injection molding; and one of the two apertures which are respectively formed on the pair of walls is formed so that at least one mold piece of a mold for injection molding the rotational steering knob can be removed through the one of the two apertures.

Preferably, the outer peripheral wall includes a plurality of hollow projecting portions which extend radially outwards perpendicularly to the rotational axis.

Preferably, the mold includes a first mold piece group for forming an outer surface of the rotational steering knob; a second mold piece group, positioned in an inner space of the rotational steering knob, for forming inner surfaces of the plurality of hollow projecting portions; and a third mold piece group, positioned in the inner space, for positioning the second mold piece group at a predetermined position in the inner space. The third mold piece group is taken out of the inner space via the one of the two apertures, subsequently the second mold piece group is moved to a position in the inner space where the second mold piece group can be taken out of the inner space via the one of the two apertures, and subsequently the second mold piece group is taken out of the inner space via the one of the two apertures.

Preferably, the endoscope further includes at least one locking device which can be manually operated from an outside of the endoscope to lock the at least one rotational steering knob; wherein at least one element of the locking device is positioned in the inner space of the at least one rotational steering knob. The at least one element of the locking device can be dismounted from the inner space via the one of the two apertures.

Preferably, at least one annular sealing member is provided for sealing a gap between the one of the two apertures and the at least one element of the locking device.

In an embodiment, the endoscope further includes a rotational center-shaft about which the at least one rotational steering knob is turned, and at least one control shaft including a cylindrical portion rotatably fitted on the rotational center-shaft and a plate portion extending perpendicular to an axis of the rotational center-shaft;
wherein the plate portion is fixed to an inner surface of one of the pair of walls, the inner surface being positioned in an inner space of the at least one rotational steering knob.

Preferably, the inner surface of the one of the two separate walls, to which the plate portion is fixed, includes a plurality of projections, wherein a corresponding plurality of holes are formed on the plate portion. The plurality of projections are firstly fitted in the corresponding plurality of holes, respectively, and subsequently a tip of each of the plurality of projections is melted by heat to fix the plate portion to the one of the two separate walls.

Preferably, the at least one control shaft is made of metal.

According to another aspect of the present invention, an endoscope is provided, including an insertion portion provided at a distal end thereof with a steerable bendable portion, and at least one rotational steering knob which is turned manually about a rotational center-shaft to bend the steerable bendable portion so as to direct a tip thereof toward a target. The at least one rotational steering knob is made of a resin material and includes a pair of walls which are separate from each other in a direction of a rotational axis of the at least one rotational steering knob, an aperture being formed on each of the pair of walls, and an outer peripheral wall which extends to connect the pair of walls so as to form the at least one rotational steering knob as a hollow knob. The endoscope further includes at least one control shaft including a cylindrical portion fitted rotatably on the rotational shaft and a plate portion. The plate portion is fixed to an inner surface of one of the pair of walls, the inner surface being positioned in an inner space of the rotational steering knob.

According to another aspect of the present invention, an endoscope includes an operational body having an insertion portion extending therefrom, and at least one non-slip rubber member fixed to an external surface of the operational body.

Preferably, the non-slip rubber member is a rubber strip.

In an embodiment, the operational body includes a grip portion, the non-slip rubber member being fixed to an external surface of the grip portion.

Preferably, the insertion portion includes a steerable bendable portion. The operational body includes at least one rotational steering knob which is turned manually to bend the steerable bendable portion so as to direct a tip thereof toward a target, the non-slip rubber member being fixed to an external surface of the rotational steering knob.

In an embodiment, the non-slip rubber member is made of a fluorine-contained rubber. Alternatively, the non-slip rubber member is made of silicone rubber.

In an embodiment, the non-slip rubber member is made of a rubber which has an outstanding performance in chemical resistance.

Preferably, the operational body includes a groove formed on an external surface of the operational body, the non-slip rubber member being fitted in the groove. According to another aspect of the present invention, an endoscope is provided, including an operational body having at least one rotational control knob; and at least one non-slip rubber member fixed to an external surface of the operational body.

The present disclosure relates to subject matter contained in the following three Japanese Patent Applications No. 2000-117681 (filed on Apr. 19, 2000), No. 2000-187801 (filed on Jun. 22, 2000) and No. 2000-256075 (filed on Aug. 25, 2000) which are expressly incorporated herein by reference in their entireties.

BRIEF DESCRIPTION OF THE DRAWINGS

The present invention will be described below in detail with reference to the accompanying drawings in which.

DESCRIPTION OF THE PREFERRED EMBODIMENTS

FIGS. 1 through 13 show the first embodiment of a control device of an endoscope 10.

Figure 1:
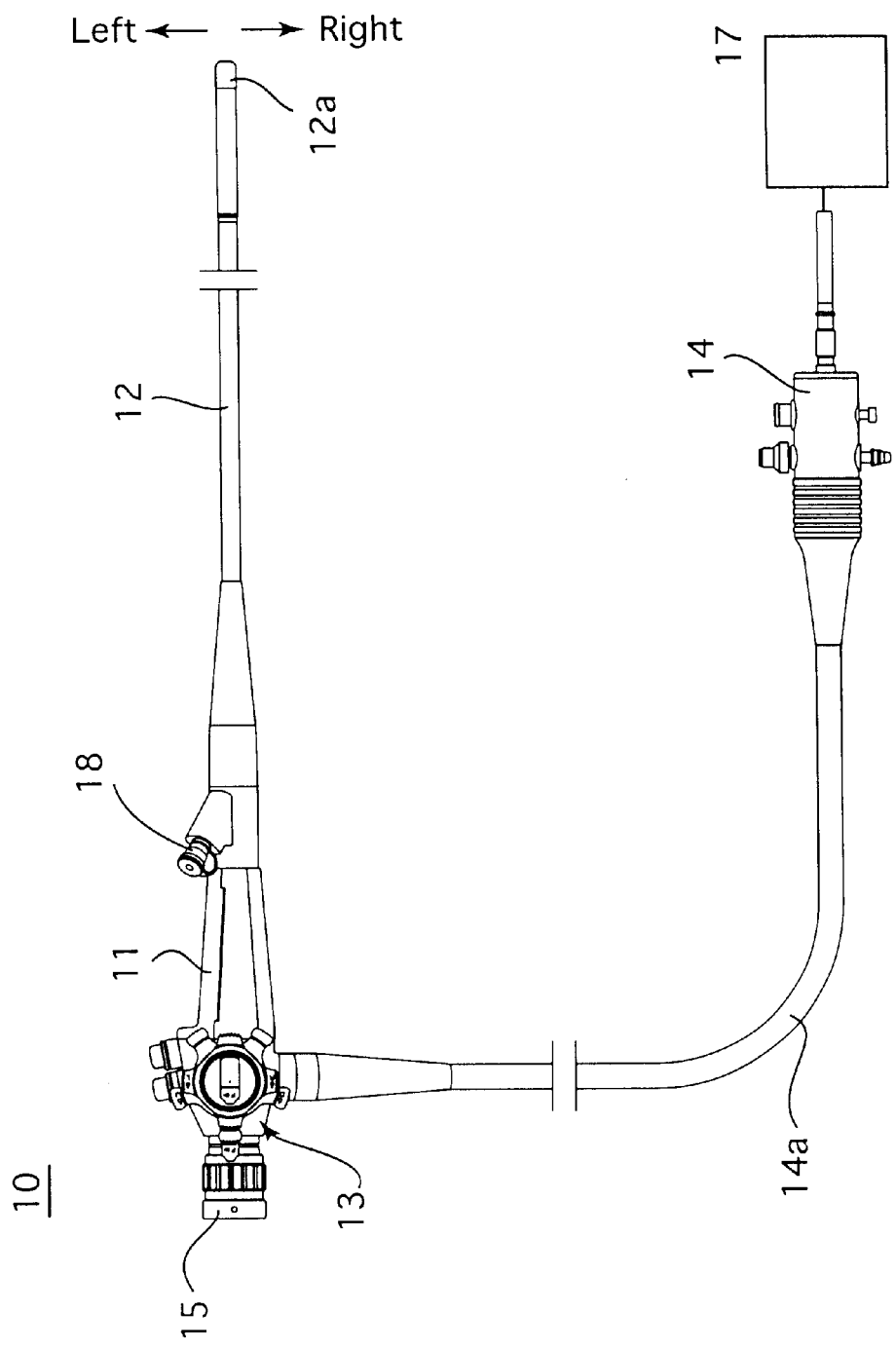
FIG. 1 is an external view of an endoscope having the first embodiment of a control device to which the present invention is applied, showing the overall structure of the endoscope.

The endoscope 10 shown in FIG. 1 is a medical device. The endoscope 10 is provided with a operational body (hollow operational body) 11 and an insertion portion 12 connected to the operational body 11. The distal end of the insertion portion 12 is formed as a (steerable) bendable portion 12a which can be steered to bend right, left, upward and downward by controlling a steering device 13 provided on the operational body 11.

The bendable portion 12a is provided at the tip thereof with an objective lens portion (not shown) and a light guide portion (not shown). Images of the object to be viewed via the objective lens portion are viewed through an eyepiece portion 15 provided at the rear end (the left end as viewed in FIG. 1) of the operational body 11. Illumination light for illuminating a target part is emitted from a lighting device 17 connected to a connector 14 of the endoscope to the light guide portion provided at the tip of the bendable portion 12a via a light-guide flexible tube 14a. The endoscope 10 is provided between the operational body 11 and the insertion portion 12 with a treatment tool insertion opening 18. The tip of a treatment tool (not shown) which is inserted into a treatment tool insertion channel in the insertion portion 12 via the treatment tool insertion opening projects out of the tip of the treatment tool insertion channel at the tip of the bendable portion 12a.

Figure 2:
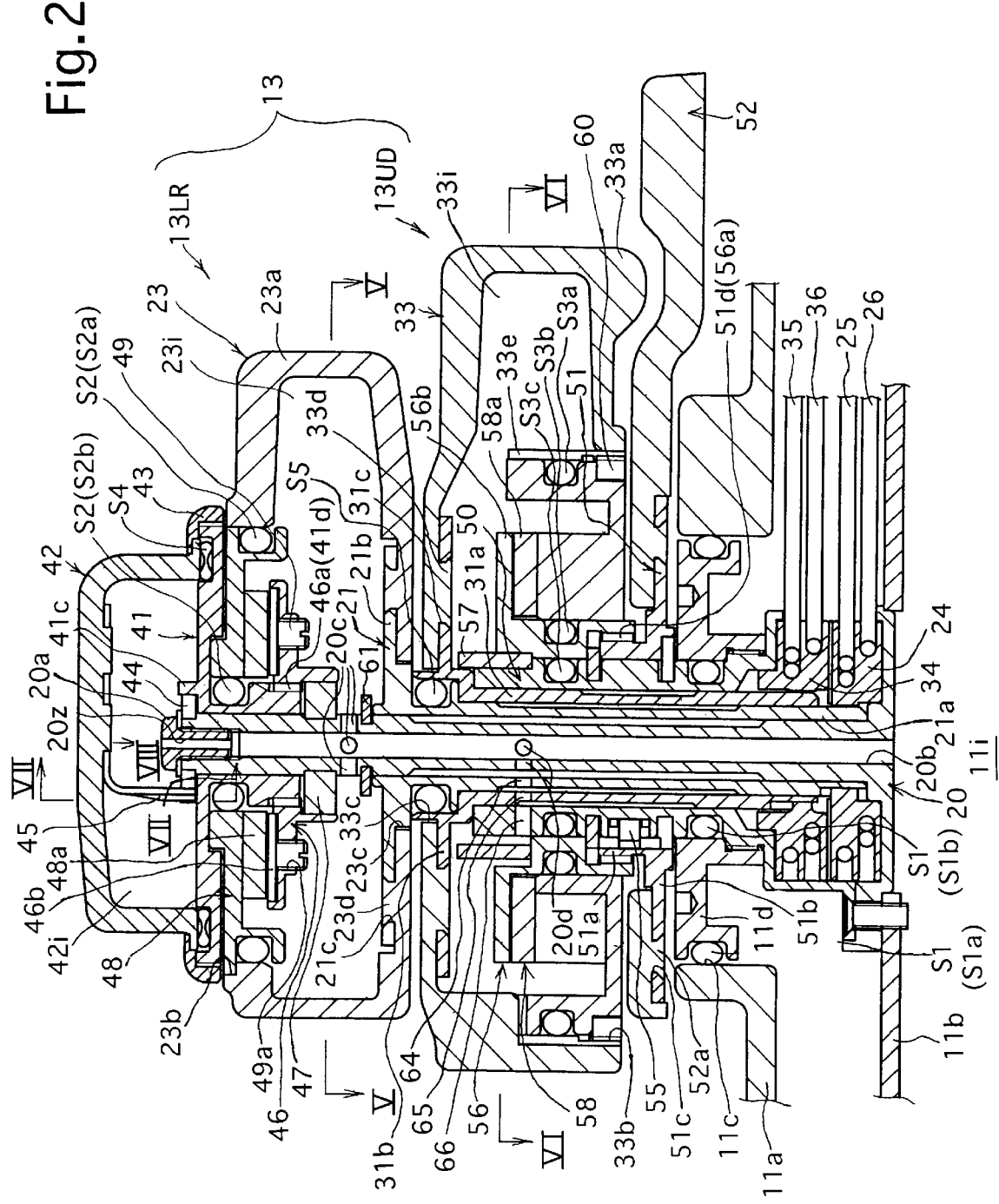
FIG. 2 is a cross sectional view of fundamental portion of the endoscope shown in FIG. 1, showing fundamental elements of the control device of the endoscope.
Figure 3:
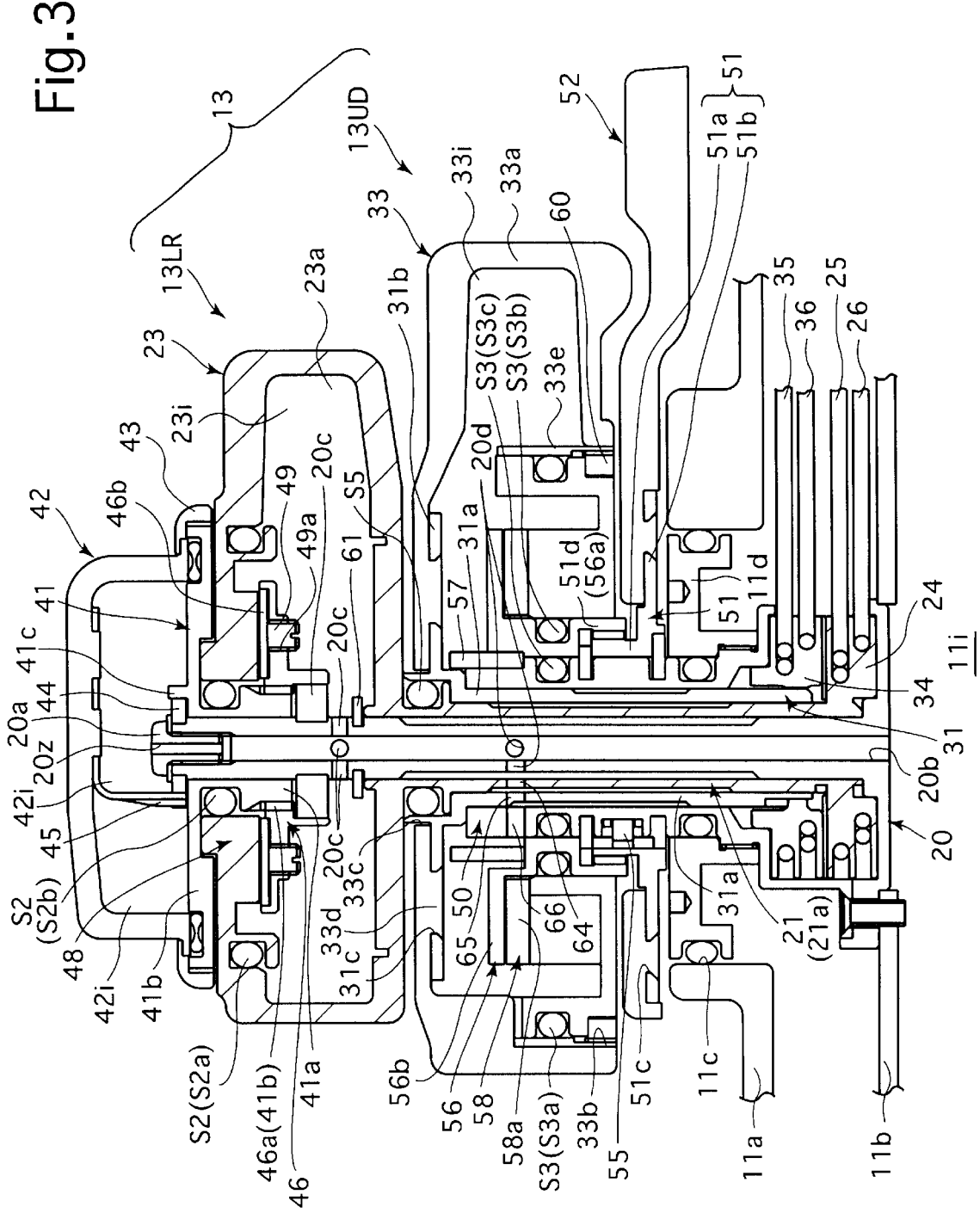
FIG. 3 is a view similar to FIG. 2 and illustrates elements of an L-R steering device which rotate together in the same rotational direction by the same angle of rotation as an integral element for the purpose of illustration.
Figure 4:
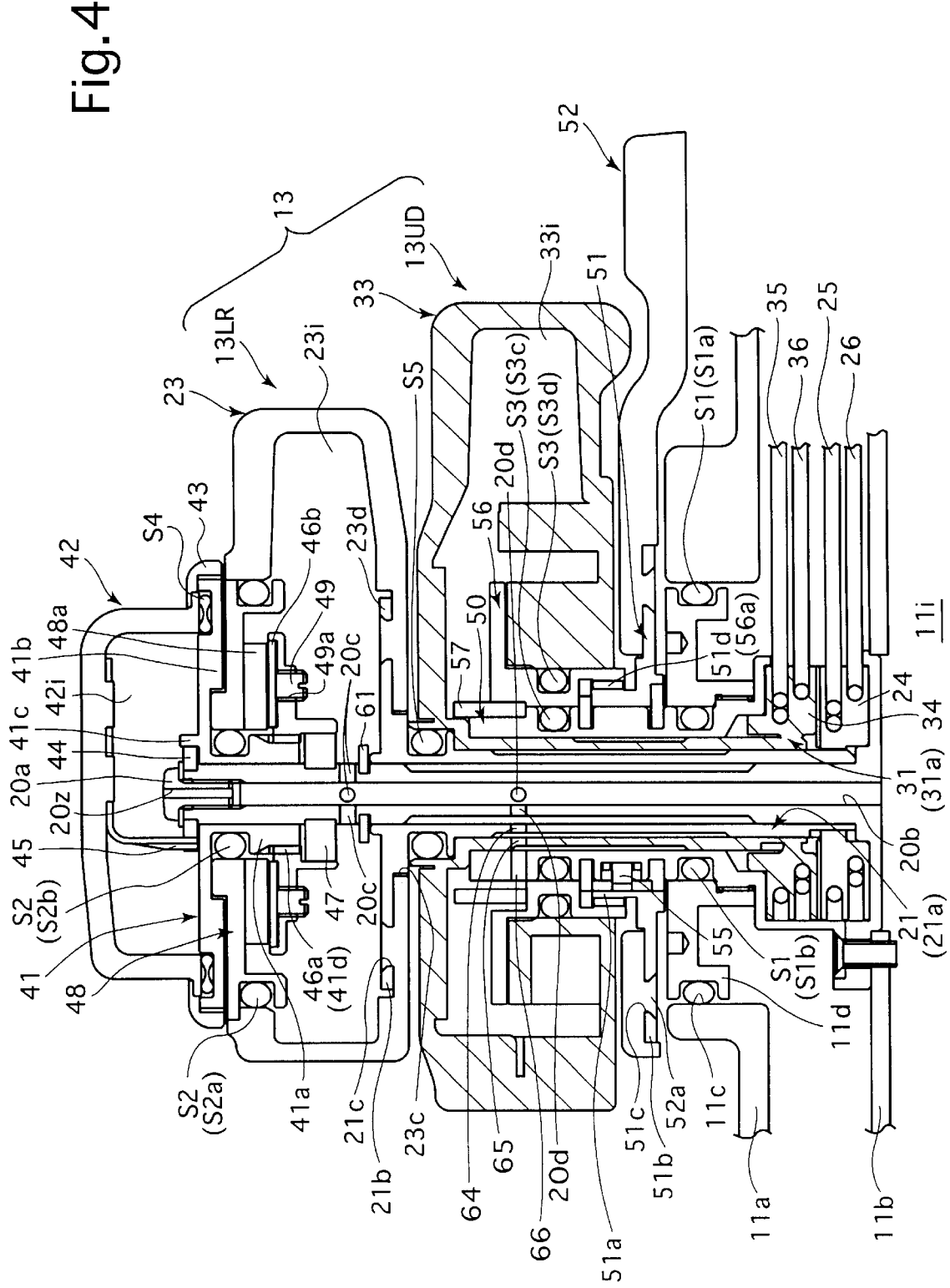
FIG. 4 is a view similar to FIG. 2 and illustrates elements of a U-D steering device which rotate together in the same rotational direction by the same angle of rotation as an integral element for the purpose of illustration.

FIG. 2 is a cross sectional view of fundamental portion of the endoscope 10, showing the steering device 13 and peripheral elements in cross section. The steering device 13 is provided with an L-R steering device 13LR for bending the bendable portion 12a left and right and a U-D steering device 13UD for bending the bendable portion 12a upward and downward. In FIG. 3, elements of the L-R steering device 13LR which rotate together are illustrated as an integral element for the purpose of illustration. In FIG. 4, elements of the U-D steering device 13UD which rotate together are illustrated as an integral element for the purpose of illustration. In FIG. 3 only the elements of the L-R steering device 13LR which rotate together are hatched. Likewise, in FIG. 4 only the elements of the U-D steering device 13UD which rotate together are hatched. Firstly, the L-R steering device 13LR will be hereinafter discussed in detail.

The operational body 11 is provided with a housing 11a which a substrate 11b is positioned in and fixed to. One end (the lower end as viewed in FIG. 2) of a rotational shaft (hollow shaft/rotational center-shaft) 20 is fixed to the substrate 11b. The rotational shaft 20 extends upwards as viewed in FIG. 2 through a through hole 11c formed on the housing 11a. An annular gap between the rotational shaft 20 and the through hole 11c is closed by a covering member 11d positioned between a stationary hollow cylindrical base 50 and the housing 11a.

The L-R steering device 13LR is provided around the rotational shaft 20 with an inner control shaft 21 rotatably fitted on the rotational shaft 20. The inner control shaft 21 is made of metal and is provided with a cylindrical shaft portion (cylindrical member) 21a and a disk portion (plate portion) 21b. The cylindrical shaft portion 21a is coaxial to the rotational shaft 20 and fitted on the rotational shaft 20. The disk portion 21b is positioned at the upper end of the cylindrical shaft portion 21a. The disk portion 21b is provided with a plurality of circular holes 21c (see FIG. 5) at equi-angular intervals about the axis of the rotational shaft 20.

Figure 5:
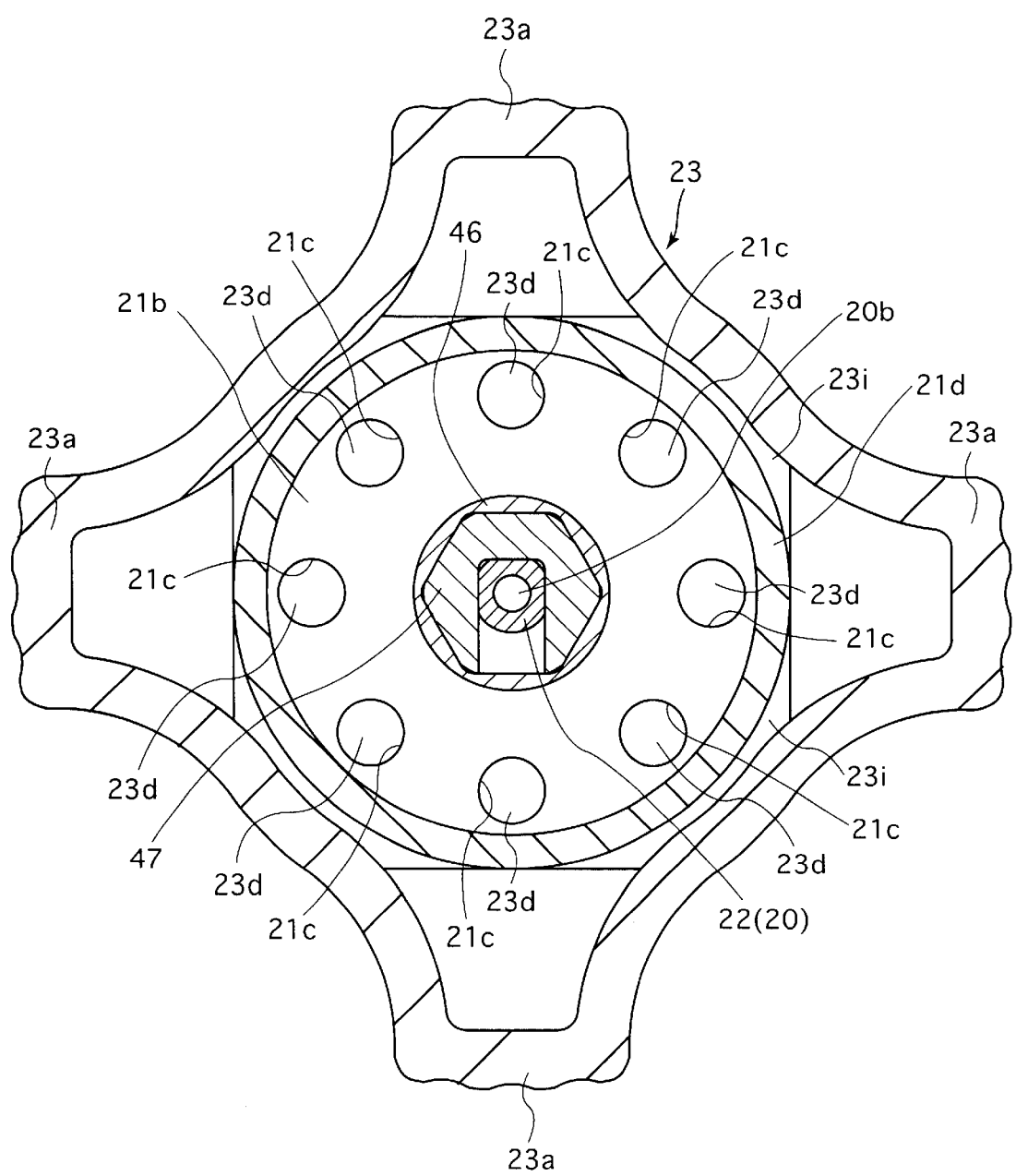
FIG. 5 is a cross sectional view of the first embodiment of the control device of the endoscope shown in FIG. 2, taken along V—V line in FIG. 2, viewed in the direction of the appended arrows.

The L-R steering device 13LR is provided with an L-R angle knob (hollow rotational control knob/rotational steering knob) 23 that is made of plastic. The L-R angle knob 23 is fixed to the inner control shaft 21. As can be seen in FIG. 5, the L-R angle knob 23 is provided at equi-angular intervals with four projecting portions 23a which extend radially outwards so that the operator can securely hold and turn the L-R angle knob 23 with his or her fingers engaging with the projecting portions 23a. The L-R angle knob 23 is formed as a hollow element as shown in FIGS. 2 through 4. The L-R angle knob 23 is provided on top and bottom portions thereof with an upper large circular aperture 23b and a lower small circular aperture 23c which have a large diameter and a small diameter, respectively. The disk portion 21b is fitted in the lower small aperture 23c. The L-R angle knob 23 is provided, on the bottom portion thereof in the vicinity of the lower small aperture 23c, with a plurality of projections 23d at equi-angular intervals about the axis of the rotational shaft 20. The plurality of projections 23d are firstly fitted in the plurality of circular holes 21c, respectively, and subsequently the tip of each projection 23d is melted by heat to fix the L-R angle knob 23 to the inner control shaft 21.

The steering device 13 is provided at the inner end (the lower end as viewed in FIG. 2) of the inner control shaft 21 with a first pulley 24 that is fixed thereto. A first pair of control wires 25 and 26 are fixed to the first pulley 24. The control wire 25 is wound around the first pulley 24 while the control wire 26 is extended from the first pulley 24 toward the distal end of the flexible insertion portion 12 if the first pulley 24 rotates in one rotational direction, and the control wire 26 is wound around the first pulley 24 while the control wire 25 is extended from the first pulley 24 toward the distal end of the flexible insertion portion 12 if the first pulley 24 rotates in the other rotational direction. The first pair of control wires 25 and 26 have respective distal portions thereof anchored to joint rings (not shown) provided in the bendable portion 12a. Pulling and extending actions of the first pair of wires 25 and 26 cause the bendable portion 12a to bend right and left. In the present embodiment, the bendable portion 12a bends left by turning the L-R angle knob 23, which is fixed to the inner control shaft 21, counterclockwise as viewed in FIG. 10, while the bendable portion 12a bends right by turning the L-R angle knob 23 clockwise as viewed in FIG. 10.

The U-D steering device 13UD will be hereinafter discussed in detail. The U-D steering device 13UD is provided around the cylindrical shaft portion 21a of the inner control shaft 21 with an outer control shaft 31 rotatably fitted on the inner control shaft 21. The outer control shaft 31 is made of metal and is provided with a cylindrical shaft portion (cylindrical member) 31a and a disk portion (plate portion) 31b. The disk portion 31b is provided with a plurality of circular holes 31c at equi-angular intervals about the axis of the rotational shaft 20.

Figure 6:
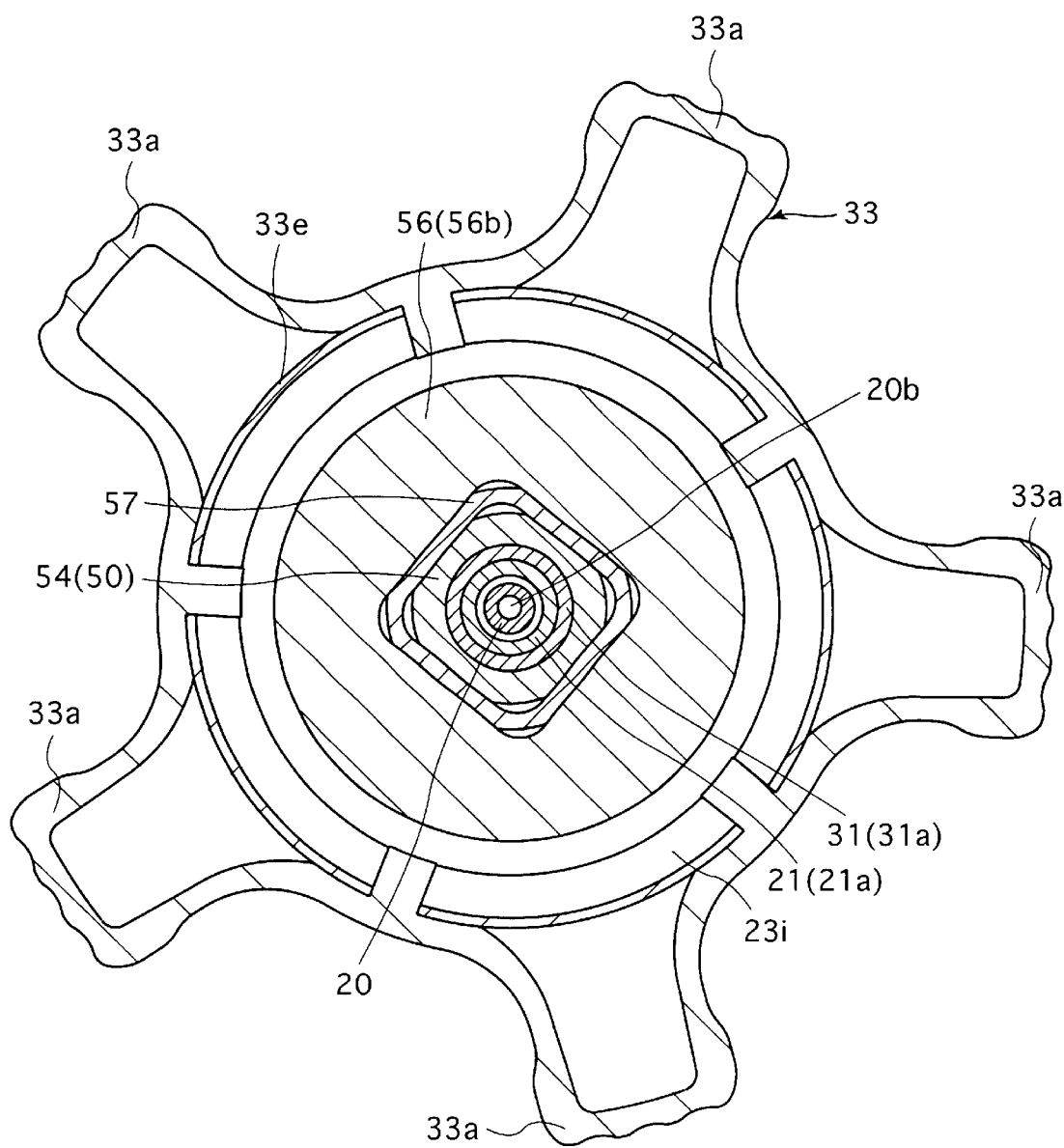
FIG. 6 is a cross sectional view of the first embodiment of the control device of the endoscope shown in FIG. 2, taken along VI—VI line in FIG. 2, viewed in the direction of the appended arrows.

The U-D steering device 13UD is provided with a U-D angle knob (hollow rotational control knob/rotational steering knob) 33 that is made of plastic. The U-D angle knob 33 is fixed to the outer control shaft 31. As can be seen in FIG. 6, the U-D angle knob 33 is provided at equi-angular intervals with five projecting portions 33a which extend radially outwards so that the operator can securely hold and turn the U-D angle knob 33 with his or her fingers engaging with the projecting portions 33a. The U-D angle knob 33 is formed as a hollow element as shown in FIGS. 2 through 4. The U-D angle knob 33 is provided on top and bottom portions thereof with an upper small circular aperture 33c and a lower large circular aperture 33b which have a small diameter and a large diameter, respectively. Part of the disk portion 31b is fitted in the upper small aperture 33c. The U-D angle knob 33 is provided, on the upper portion thereof in the vicinity of the upper small aperture 33c, with a plurality of projections 33d at equi-angular intervals about the axis of the rotational shaft 20. The plurality of projections 33d are firstly fitted in the plurality of circular holes 31c, respectively, and subsequently the tip of each projection 33d is melted by heat to fix the U-D angle knob 33 to the outer control shaft 31. A metal ring 33e having a female thread formed on an inner peripheral surface thereof is positioned in the U-D angle knob 33 in the lower large aperture 33b and is fixed to the U-D angle knob 33.

The steering device 13 is provided at the inner end (the lower end as viewed in FIG. 2) of the outer control shaft 31 with a second pulley 34 that is fixed thereto. A second pair of control wires 35 and 36 are fixed to the second pulley 34. The control wire 35 is wound around the second pulley 34 while the control wire 36 is extended from the second pulley 34 toward the distal end of the flexible insertion portion 12 if the second pulley 34 rotates in one rotational direction, and the control wire 36 is wound around the second pulley 34 while the control wire 65 is extended from the second pulley 34 toward the distal end of the flexible insertion portion 12 if the second pulley 34 rotates in the other rotational direction. The second pair of control wires 35 and 36 have respective distal portions thereof anchored to the joint rings (not shown) provided in the bendable portion 12a. The pulling and extending actions of the second pair of wires 35 and 36 cause the bendable portion 12a to bend upward and downward. In the present embodiment, the bendable portion 12a bends upward by turning the U-D angle knob 33, which is fixed to the outer control shaft 31, counterclockwise as viewed in FIG. 10, while the bendable portion 12a bends downward by turning the U-D angle knob 33 clockwise as viewed in FIG. 10.

Each of the L-R angle knob 23 and the U-D angle knob 33 is locked with a corresponding locking device to fix the bendable portion 12a to a desired curved shape, i.e., to fix the orientation of the tip of the bendable portion 12a. Firstly, the locking device for the L-R steering device 13LR will be hereinafter discussed in detail.

Figure 7:
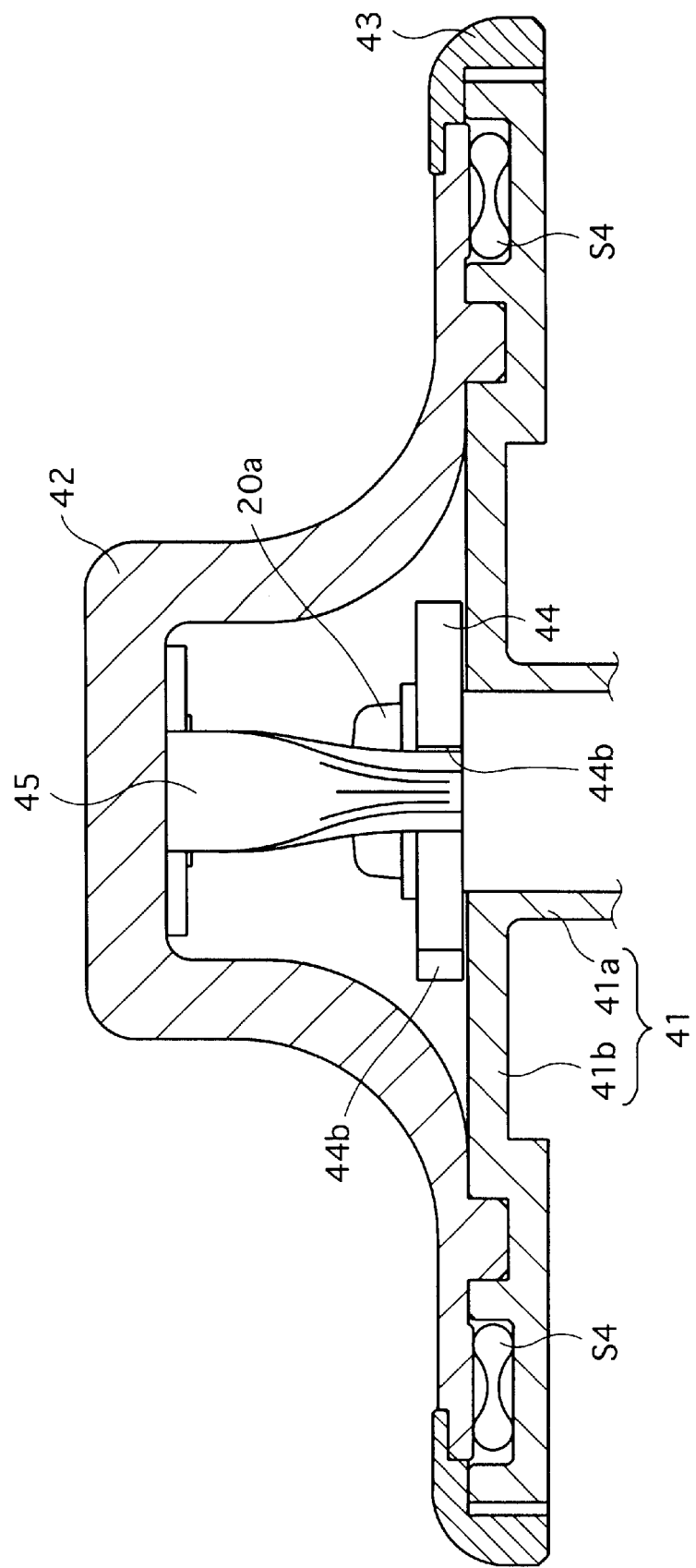
FIG. 7 is a cross sectional view of the first embodiment of the control device of the endoscope shown in FIG. 2, taken along VII—VII line in FIG. 2, viewed in the direction of the appended arrows.
Figure 9:
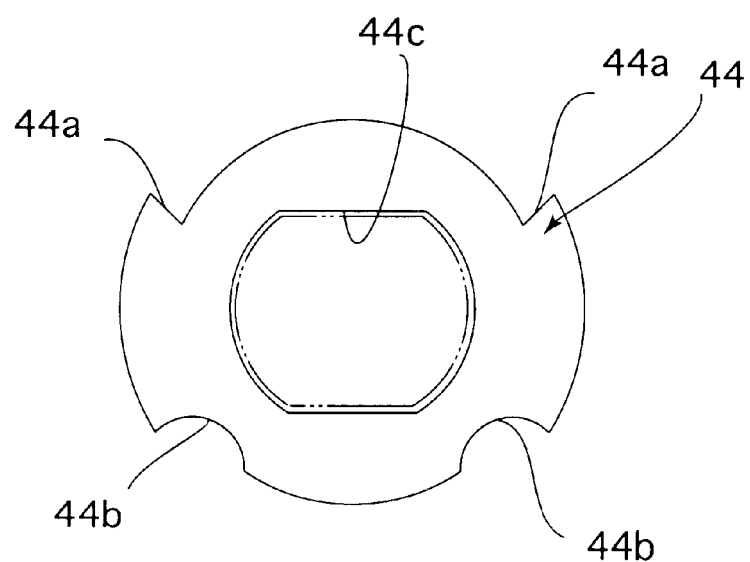
FIG. 9 is a plan view of the retaining ring shown in FIG. 8.
Figure 10:
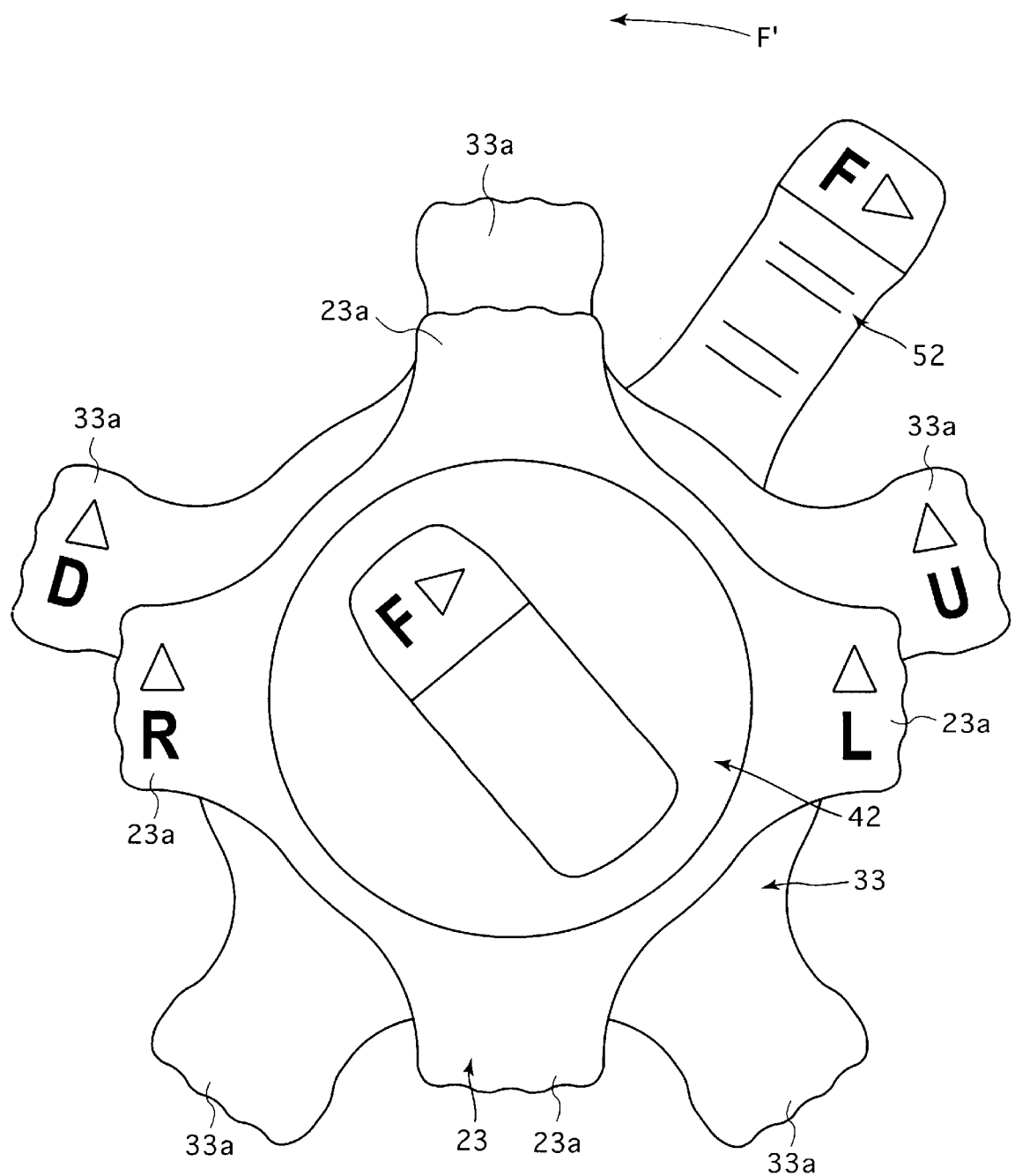
FIG. 10 shows a plan view of the control device of the endoscope shown in FIG. 1.
Figure 11:
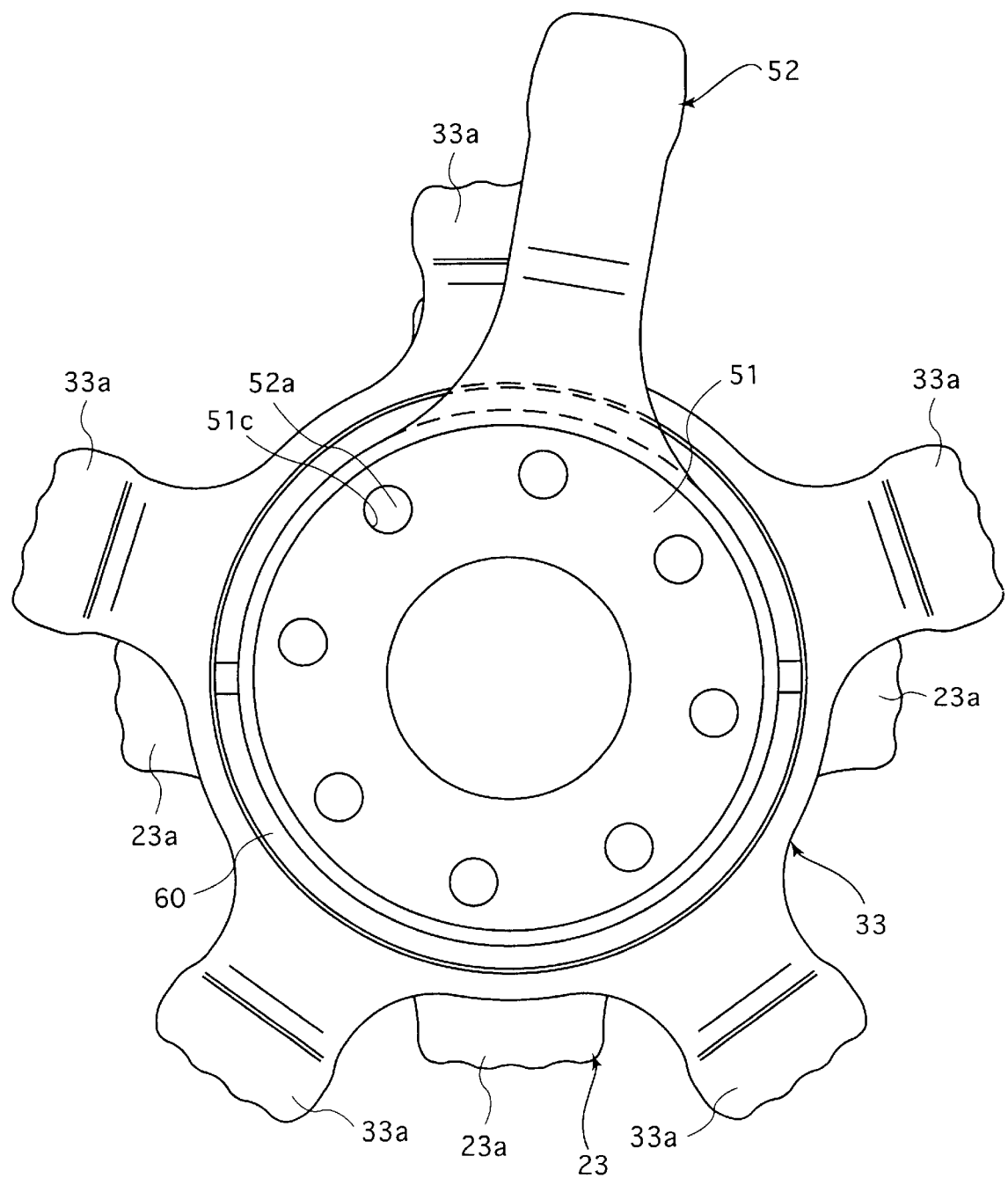
FIG. 11 shows a bottom view of fundamental elements of the control device of the endoscope shown in FIG. 1.
Figure 12:
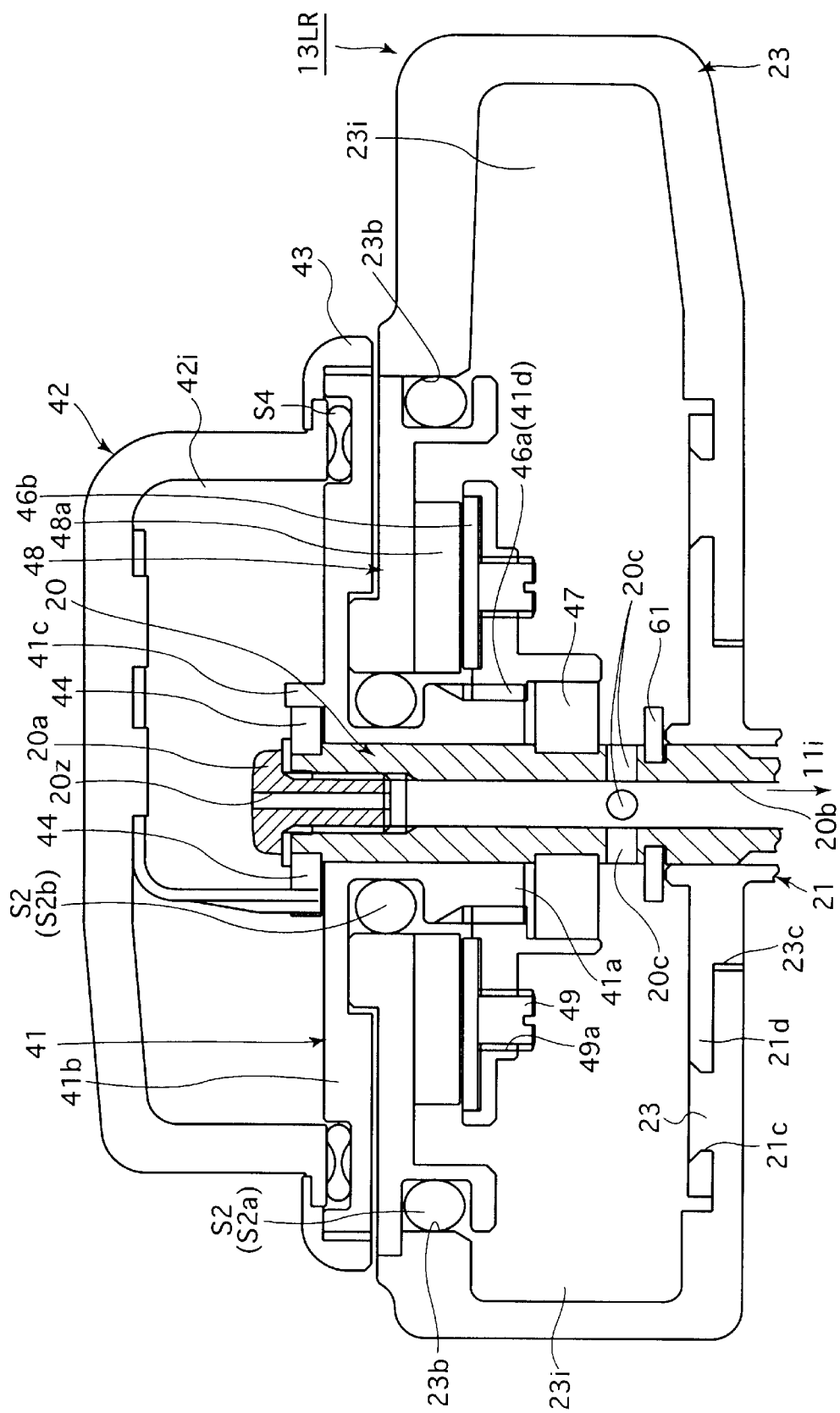
FIG. 12 is a cross sectional view of fundamental portion of the endoscope shown in FIG. 1, showing fundamental elements of the L-R steering device.
Figure 13:
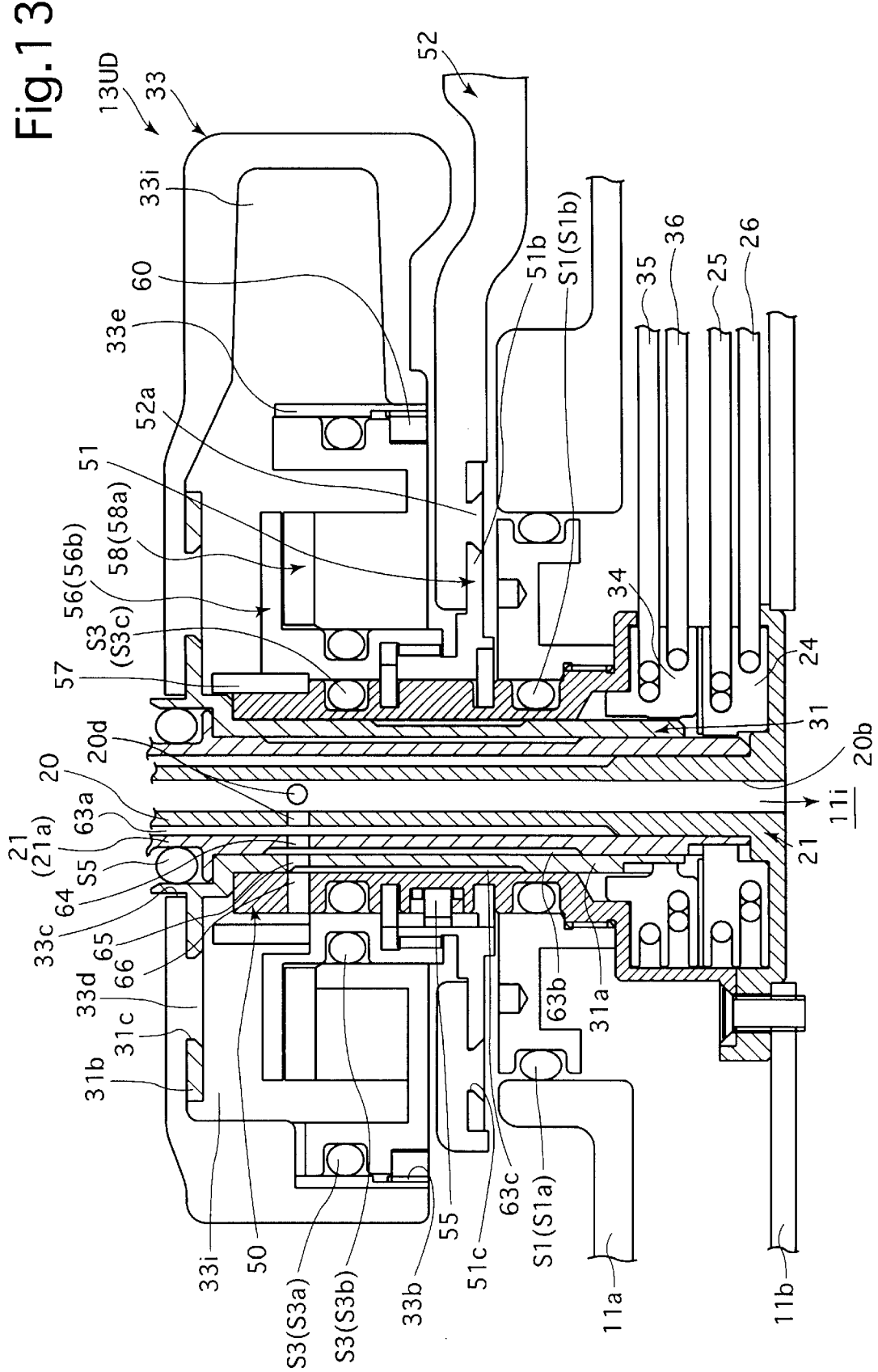
FIG. 13 is a cross sectional view of fundamental portion of the endoscope shown in FIG. 1, showing fundamental elements of the U-D steering device.

A first rotating member 41 which includes a cylindrical portion 41a and a disk portion 41b is fixed at the upper end of the rotational shaft 20 (see FIG. 7). The cylindrical portion 41a is fitted on the upper end of the rotational shaft 20 to be rotatable relative to the rotational shaft 20, so that the rotational member 41 is rotatable about the rotational shaft 20. An L-R lock knob (hollow rotational control knob) 42 is fixedly mounted onto the disk portion 41b via a fixing ring 43. The fixing ring 43 is provided on an inner peripheral surface thereof with a female thread, while the outer edge of the disk portion 41b is provided with a male thread which can be engaged with the female thread of the fixing ring 43. The fixing ring 43 is fixed to the disk portion 41b via the male and female threads to fix the L-R lock knob 42 to the rotational member 41. Accordingly, the first rotating member 41 rotates together with the L-R lock knob 42 when the L-R lock knob 42 is turned manually. A retaining ring 44 for preventing the rotational member 41 and the L-R lock knob 42 that is integral with the rotational member 41 from coming off the rotational shaft 20 is fixed at the upper end of the rotational shaft 20. As shown in FIG. 9, the retaining ring 44 is provided at the center thereof with a non-circular hole 44c, while the upper end of the rotational shaft 20 is formed to have a cross sectional shape which corresponds to the shape of the non-circular hole 44c. Due to this structure, the retaining ring 44 is fitted on the upper end of the rotational shaft 20 while being prohibited from rotating about the axis of the rotational shaft 20 relative to the rotational shaft 20. The retaining ring 44 is secured to the upper end of the rotational shaft 20 via a set screw 20a that is screwed into the upper end of the rotational shaft 20. Accordingly, the set screw 20a prevents the retaining ring 44 from coming off the upper end of the rotational shaft 20.

Figure 8:
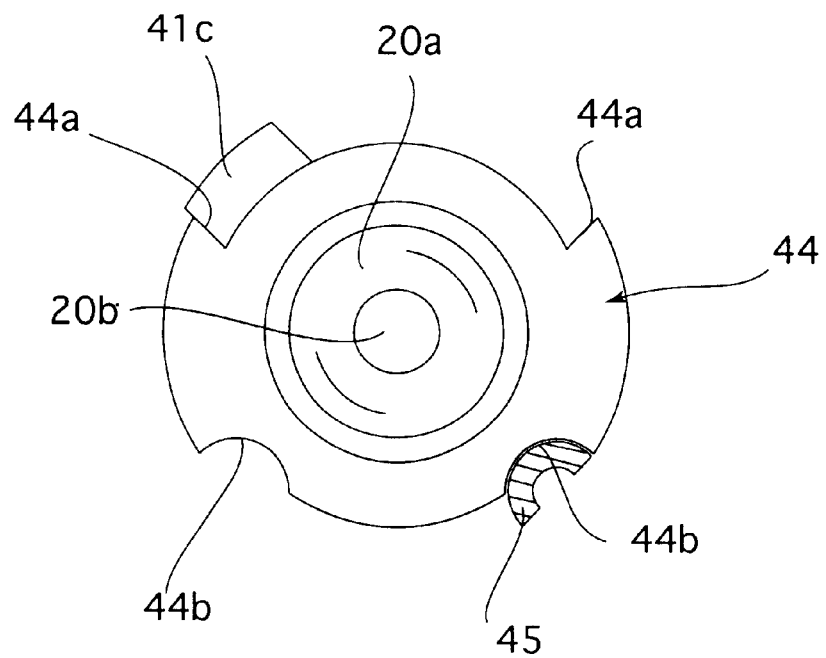
FIG. 8 is a plan view of part of the first embodiment of the control device of the endoscope shown in FIG. 2, showing a retaining ring, a set screw and other peripheral elements, viewed in the direction of an arrow VIII shown in FIG. 8.

As can be understood from FIGS. 7 through 9, the integral member which includes the first rotating member 41 and the L-R lock knob 42 can rotate within a predetermined range of rotation which is defined by a projection 41c projected from the disk portion 41b and two stop faces 44a formed on the retaining ring 44 at different circumferential positions thereof. The projection 41c abuts against one of the two stop faces 44a when the first rotating member 41 rotates to one end of the predetermined range thereof, while the projection 41c abuts against the other stop face 44a when the first rotating member 41 rotates to the other end of the predetermined range thereof. Accordingly, the predetermined range corresponds to a movable range of the projection 41c between the two stop faces 44a. The retaining ring 44 is further provided with two stop recesses 44b which are positioned substantially on the opposite sides from the two stop faces 44a with respect to the axis of the rotational shaft 20 in radial directions thereof, respectively. An engaging spring 45 (see FIGS. 7, 8 and 12) which is fixed to the L-R lock knob 42 engages with a stop recess 44b with a click when the projection 41c abuts against a stop face 44a, the two stop faces 44a determining two stop positions of the integral member which includes the first rotating member 41 and the L-R lock knob 42, respectively.

The cylindrical portion 41a of the first rotating member 41 is provided on an outer peripheral surface thereof with a male thread 41d. The locking device for the L-R steering device 13LR is provided inside the L-R angle knob 23 with an axially-movable lock member 46. The axially-movable lock member 46 is positioned around the rotational shaft 20 and is provided on an inner peripheral surface thereof with a female thread 46a which is in mesh with the male thread 41d of the cylindrical portion 41a. As shown in FIG. 5, the rotational shaft 20 is partly formed as a non-cylindrical portion 22 having a non-circular cross section. A removable retaining member 47 having a generally hexagonal section is fitted on the non-cylindrical portion 22 at the bottom of the axially-movable lock member 46, and is coupled to the axially-movable lock member 46 in a non-rotatable manner relative to the axially-movable lock member 46 to prevent the axially-movable lock member 46 from rotating relative to the rotational shaft 20. Thus, the axially-movable lock member 46 rotates together with the rotational shaft 20. Accordingly, turning the L-R lock knob 42 causes the axially-movable lock member 46 to move along the axis of the rotational shaft 20 without rotating about the rotational shaft 20 due to the engagement of the male thread 41d with the female thread 46a.

If the axially-movable lock member 46 moves up and down by rotation of the integral member which includes the first rotating member 41 and the L-R lock knob 42, a first friction pad 46b which is fixed to an upper face of the axially-movable lock member 46 is engaged with and disengaged from a second friction pad 48a fixed to an axially-immovable lock member 48. Each of the first and second friction pads 46b and 48a is in the shape of a disk. The first friction pad 46b can be made of a material having a high coefficient of friction such as cork or silicone rubber, while the second friction pad 48a can be made of, for example, metal (e.g., stainless steel). The axially-immovable lock member 48 is formed as part of the L-R angle knob 23 in such a manner as to cover the upper large circular aperture 23b of the L-R angle knob 23. The axially-immovable lock member 48 rotates together with the inner control shaft 21 and the L-R angle knob 23 when the L-R angle knob 23 is turned. If the first friction pad 46b is brought into pressing contact with the second friction pad 48a by an upward movement of the axially-movable lock member 46, the rotation of the axially-immovable lock member 48 is restricted by friction generated between the first and second friction pads 46b and 48a. If the axially-immovable lock member 48 is locked via the first and second friction pads 46b and 48a, the integral member which includes the first rotating member 41 and the L-R lock knob 42 is prohibited from rotating, so that the first pulley 24 is also prohibited from rotating. As a result, the bendable portion 12a is prohibited from bending right and left, so that the bendable portion 12a can be fixed to a desired curved shape in left or right direction. More specifically, turning the L-R lock knob 42 in the direction of an arrow F' or a locking force applying direction (i.e., counterclockwise as viewed in FIG. 10) causes the axially-movable lock member 46 to move upward to bring the first friction pad 46b into pressing contact with the second friction pad 48a to thereby restrict the rotation of the L-R angle knob 23. On the other hand, turning the L-R lock knob 42 in the direction shown by a triangular arrow "Δ" and a letter "F" which are printed on the L-R lock knob 42 or a locking force releasing direction (i.e., clockwise as viewed in FIG. 10) causes the axially-movable lock member 46 to move downward to disengage the first friction pad 46b from the second friction pad 48a to thereby allow the L-R angle knob 23 to be turned freely. Although the L-R lock knob 42 stops with a click at each of the two stop positions thereof as has been described, the L-R angle knob 23 is locked when the L-R lock knob 42 stops at one of the two stop positions, while the L-R angle knob 23 is allowed to be turned when the L-R lock knob 42 stops at the other stop position. The former and latter stop positions are herein referred to as "lock position" and "unlock position", respectively. Each of the axially-movable lock member 46 and the axially-immovable lock member 48 is formed as an annular member so that the first friction pad 46b can be pressed against the second friction pad 48a regardless of the rotational position of the axially-immovable lock member 48, which rotates together with the L-R angle knob 23, relative to the axially-movable lock member 46.

The first friction pad 46b is supported on an upper face of the axially-movable lock member 46 via four adjusting screws 49 (only two are shown in FIGS. 2 through 4). The four adjusting screws 49 are arranged at equi-angular intervals about the axis of the axially-movable lock member 46 (i.e., about the axis of the rotational shaft 20), and are screwed into corresponding four threaded holes 49a (only two are shown in FIGS. 2 through 4) formed on the axially-movable lock member 46 so that the end (the upper end as viewed in FIG. 2) of each adjusting screw 49 contacts the lower face of the first friction pad 46b. With this structure, rotating each adjusting screw 49 clockwise and counterclockwise causes the first friction pad 46b to move up and down, respectively. Although the number of the adjusting screws 49 is four in this particular embodiment, three or more than four adjusting screws 49 can be arranged at equi-angular intervals about the axis of the axially-movable lock member 46 to be screwed into a corresponding plurality of threaded holes 49a formed on the axially-movable lock member 46. If the vertical position of the first friction pad 46b relative to the movable lock member 46 varies, the frictional resistance between the first and second friction pads 46b and 48a in a state where the L-R lock knob 42 stops at the lock position varies. Accordingly, the locking force applied to the L-R angle knob 23 can be adjusted by adjusting the vertical position of the first friction pad 46b relative to the movable lock member 46 via the adjusting screws 49. For instance, the frictional resistance between the first and second friction pads 46b and 48a can be set so that the bendable portion 12a is half-locked, i.e., so that the bendable portion 12a in a locked state is unlocked in accordance with the degree of an external force applied to the bendable portion 12a. Such an adjustment of the frictional resistance between the first and second friction pads 46b and 48a can be easily carried out by adjusting the vertical position of the first friction pad 46b relative to the movable lock member 46 via the adjusting screws 49.

In the following description, the locking device for the U-D steering device 13UD will be hereinafter discussed in detail.

The U-D steering device 13UD is provided around the outer control shaft 31 with the aforementioned stationary hollow cylindrical base (cylindrical member) 50, which is coaxial to the rotational shaft 20. The inner end (the lower end as viewed in FIG. 2) of the cylindrical base 50 is fixed to the substrate 11b together with the rotational shaft 20. The inner and outer control shafts 21 and 31 and the first and second pulleys 24 and 34 are held between the rotational shaft 20 and the cylindrical base 50.

A second rotating member 51 which includes a cylindrical portion 51a and a disk portion 51b is fitted on the cylindrical base 50. The cylindrical portion 51a is fitted on the cylindrical base 50 about the rotational shaft 20 to be rotatable relative to the rotational shaft 20 and to be immovable in the axial direction (the vertical direction as viewed in FIG. 2) of the rotational shaft 20 relative thereto. A U-D lock lever 52 is fixed to the disk portion 51b. The disk portion 51b is provided with a plurality of circular holes 51c at equiangular intervals about the axis of the rotational shaft 20. The U-D lock lever 52 is provided with a plurality of projections 52a at equi-angular intervals about the axis of the rotational shaft 20. The plurality of projections 52a are firstly fitted in the plurality of circular holes 51c, respectively, and subsequently the tip of each projection 52a is melted by heat to fix the U-D lock lever 52 to the second rotating member 51. Accordingly, the U-D lock lever 52 together with the second rotating member 51 is supported by the cylindrical base 50 to be rotatable about the cylindrical portion 51a (i.e., the rotational shaft 20). Unlike the hollow L-R lock knob 42, the U-D lock lever 52 is formed to extend radially in a direction perpendicular to the axis of the rotational shaft 20 so as to be easily turned manually.

An integral member which includes the second rotating member 51 and the U-D lock lever 52 can rotate within a predetermined range which is defined by a rotational range defining mechanism (not shown) provided between the cylindrical portion 51a and the cylindrical base 50. With the rotational range defining mechanism, the U-D lock lever 52 stops with a click with an engaging spring 55 at each of two stop positions corresponding to the opposite ends of the rotational range of the U-D lock lever 52.

The cylindrical portion 51*a* of the second rotating member 51 is provided on an outer peripheral surface thereof with a male thread 51*d*. The locking device for the U-D steering device 13UD is provided inside the U-D angle knob 33 with an axially-movable lock member 56. The axially-movable lock member 56 is positioned around the rotational shaft 20, and is provided on an inner peripheral surface thereof with a female thread 56*a* which is in mesh with the male thread 51*d* of the cylindrical portion 51*a*. As shown in FIG. 6, the upper end of the cylindrical base 50 is formed as a non-cylindrical portion 54 having a non-circular cross section. An annular joint member 57 which is fixed to the axially-movable lock member 56 and whose cross sectional shape substantially corresponds to that of the non-cylindrical portion 54 of the cylindrical base 50 is firmly fitted on the non-cylindrical portion 54 so that the axially-movable lock member 56 does not rotate relative to the cylindrical base 50 and the rotational shaft 20. Thus, the axially-movable lock member 56 is prohibited from rotating about the cylindrical base 50. Accordingly, turning the U-D lock lever 52 causes the axially-movable lock member 56 to move along the axis of the rotational shaft 20 without rotating about the rotational shaft 20 due to the engagement of the male and female threads 51*d* and 56*a*. The annular joint member 57 can be a member separate from the axially-movable lock member 56, or can be formed integral with the axially-movable lock member 56.

If the axially-movable lock member 56 moves up and down by rotation of the integral member which includes the second rotating member 51 and the U-D lock lever 52, a first friction pad 56*b* formed integral with the upper end of the axially-movable lock member 56 is engaged with and disengaged from a second friction pad 58*a* fixed to an axially-immovable lock member 58, respectively. Each of the first and second friction pads 56*b* and 58*a* is in the shape of a disk. The first friction pad 56*b* is made of, for example, metal (e.g., stainless steel), while the second friction pad 58*a* can be made of a material having a high coefficient of friction such as cork or silicone rubber. The axially-immovable lock member 58 is coupled to the metal ring 33*e* of the U-D angle knob 33 so that the axially-immovable lock member 58 rotates together with the U-D angle knob 33 when the U-D angle knob 33 is turned. If the first friction pad 56*b* is brought into pressing contact with the second friction pad 58*a* by a downward movement of the axially-movable lock member 56, the rotation of the axially-immovable lock member 58 is restricted by friction generated between the first and second friction pads 56*b* and 58*a*. If the axially-immovable lock member 58 is locked via the first and second friction pads 56*b* and 58*a*, an integral member which includes the outer control shaft 31 and the U-D angle knob 33 is prohibited from rotating, so that the second pulley 34 is also prohibited from rotating. As a result, the bendable portion 12*a* is prohibited from bending upward and downward, so that the bendable portion 12*a* can be fixed to a desired curved shape in an upward or downward direction. More specifically, turning the U-D lock lever 52 in the direction of the arrow F' or a lock-applying direction (i.e., counterclockwise as viewed in FIG. 10) causes the axially-movable lock member 56 to move downward to bring the first friction pad 56*b* into pressing contact with the second friction pad 58*a* to thereby restrict the rotation of the U-D angle knob 33. On the other hand, turning the U-D lock lever 52 in the direction shown by a triangular arrow "Δ" and a letter "F" which are printed on the U-D lock lever 52, or a lock-releasing direction (i.e., clockwise as viewed in FIG. 10) causes the axially-movable lock member 56 to move upward to disengage the first friction pad 56*b* from the second friction pad 58*a* to thereby allow the U-D angle knob 33 to be turned freely. Although the U-D lock lever 52 stops with a click at each of the two stop positions thereof as has been described, the U-D angle knob 33 is locked when the U-D lock lever 52 stops at one of the two stop positions, and the U-D angle knob 33 is allowed to be turned when the U-D lock lever 52 stops at the other stop position. The former and latter stop positions are herein referred to as "lock position" and "unlock position", respectively. Each of the axially-movable lock member 56 and the axially-immovable lock member 58 is formed as an annular member so that the first friction pad 56*b* can be pressed against the second friction pad 58*a* regardless of the rotational position of the axially-immovable lock member 58, which rotates together with the U-D angle knob 33, relative to the axially-movable lock member 56.

The axially-immovable lock member 58 is fitted in the metal ring 33*e*, which is fixed to the U-D angle knob 33, so that the axial position of the axially-immovable lock member 58 can be adjusted relative to the metal ring 33*e*. A female thread 33*k* formed on an inner peripheral surface of the metal ring 33*e* is in mesh with a male thread 60*a* formed on an outer peripheral surface of an adjusting ring 60 (see FIG. 13). This adjusting ring 60 supports the axially-immovable lock member 58 from the bottom thereof. If the adjusting ring 60 is rotated in a state where the integral member which includes the outer control shaft 31 and the U-D angle knob 33 is held so as not to rotate relative to the rotational shaft 20, the vertical position (i.e., the vertical position as viewed in FIG. 2) of the adjusting ring 60 relative to the metal ring 33*e* can be adjusted due to the engagement of the female thread 33*k* with the male thread 60*a*. Accordingly, the vertical position of the axially-immovable lock member 58 relative to the axially-movable lock member 56 can be adjusted by rotating the adjusting ring 60 relative to the metal ring 33*e*. If the vertical position of the axially-immovable lock member 58 relative to the axially-movable lock member 56 can be adjusted, the locking force applied to the U-D angle knob 33 can be adjusted since the frictional resistance between the first and second friction pads 56*b* and 58*a* in a state where the U-D lock lever 52 stops at the lock position varies. For instance, the frictional resistance between the first and second friction pads 56*b* and 58*a* can be set so that the bendable portion 12*a* is half-locked, i.e., so that the bendable portion 12*a* in a locked state is unlocked in accordance with the degree of an external force applied to the bendable portion 12*a*. Such an adjustment of the frictional resistance between the first and second friction pads 56*b* and 58*a* can be easily carried out by adjusting the vertical position of the axially-immovable lock member 58 relative to the axially-movable lock member 56 by rotating the adjusting ring 60.

The above described elements of each of the L-R steering device 13LR and the U-D steering device 13UD are assembled about the rotational shaft 20 during assembly of the steering device 13. The U-D steering device 13UD is held between the disk portion 21*b* of the inner control shaft 21 and the first pulley 24, which are elements of the L-R steering device 13LR, so that the vertical position of the U-D steering device 13UD is determined by the disk portion 21*b* and the first pulley 24. The rotational shaft 20 is provided between the opposite ends thereof with an annular groove in which a retaining member 61 is fitted. The retaining member 61 is engaged with the upper end of the inner control shaft 21. With this structure, the U-D steering device 13UD and the integral member which includes the inner control shaft 21 and the L-R angle knob 23 are prevented from coming off the rotational shaft 20. The integral member which includes the first rotating member 41 and the L-R lock knob 42, which is positioned above the L-R angle knob 23, is prevented from coming off the rotational shaft 20 due to the aforementioned retaining ring 44. Accordingly, the whole of the steering device 13 (13LR and 13UD) is supported by the rotational shaft 20 so as not to come off the rotational shaft 20.

The steering device 13 is provided therein with a plurality of sealing members (e.g., elastic O-rings) for preventing any foreign matter (e.g., water, moisture, dust and the like) from entering into the steering device 13. Such a plurality of sealing members include first through fifth sealing member groups S1, S2, S3, S4 and S5. The housing 11a is sealed with the first sealing member group S1. The L-R angle knob 23 is sealed with the second sealing member group S2. The U-D angle knob 33 is sealed with the third sealing member group S3. The L-R lock knob 42 is sealed with the fourth sealing member group S4. The outer control shaft 31 is sealed with respect to the inner control shaft 21 with the fifth sealing member group S5. For instance, in the case where the endoscope 10 is immersed in a disinfecting solution, all the external surfaces of the endoscope 10 are properly disinfected while completely preventing the disinfecting solution from entering into the hollow L-R angle knob 23, the hollow U-D angle knob 33, the hollow L-R lock knob 42 and the housing 11a.

The L-R angle knob 23 is a bottomed hollow substantially cylindrical member having an inner space 23i. The upper large aperture 23b and the lower small aperture 23c are formed on the upper and lower ends of the L-R angle knob 23, respectively. The disk portion 21b of the inner control shaft 21 is fitted in the small aperture 23c in a watertight fashion. An assembly of fundamental elements of the locking device for locking the L-R angle knob 23 (e.g., the first rotating member 41, the axially-movable lock member 46 and the axially-immovable lock member 48) is positioned to cover and close the upper large aperture 23b in a watertight fashion via the second and fourth sealing member groups S2 and S4. The second sealing member group S2 includes a first sealing member S2a which seals a gap between an outer peripheral face of the axially-immovable lock member 48 and an inner peripheral face of the L-R angle knob 23, and a second sealing member S2b which seals a gap between the axially-immovable lock member 48 and the cylindrical portion 41a of the first rotating member 41.

The L-R lock knob 42, which locks the L-R angle knob 23 when turned to the lock position of the L-R lock knob 42, is formed as a hollow member having an inner space 42i whose bottom end is closed by the disk portion 41b of the first rotating member 41. The fourth sealing member group (O-ring) S4 is disposed in a gap between the disk portion 41b of the first rotating member 41 and the L-R lock knob 42 to prevent any fluid from entering into the inner space 42i via the gap. Since the inner space 42i is made watertight with the fourth sealing member group S4, fluid is prevented from entering into a gap between the first rotating member 41 and the rotational shaft 20 in the inner space 42i with the fourth sealing member group S4. Accordingly, the fourth sealing member group S4 directly functions to make the inner space 42i of the L-R lock knob 42 watertight, and to indirectly make the inner space 23i of the L-R angle knob 23 watertight.

Similar to the L-R angle knob 23, the U-D angle knob 33 is an inverted bottomed substantially cylindrical hollow member having an inner space 33i. The upper small aperture 33c and the lower large aperture 33b are formed on the upper and lower ends of the U-D angle knob 33, respectively. Part of the disk portion 31b is fitted in the upper small aperture 33c in a watertight fashion. The fifth sealing member group (an O-ring) S5 seals a gap between the outer control shaft 31 and the rotational shaft 20 in a watertight fashion. An assembly of fundamental elements of the locking device for locking the U-D angle knob 33 (e.g., the second rotating member 51, the axially-movable lock member 56 and the axially-immovable lock member 58) is positioned to cover and close the lower large aperture 33b in a watertight fashion via the third sealing member group S3. The third sealing member group S3 includes a first annular sealing member S3a which seals a gap between an outer peripheral face of the axially-immovable lock member 58 and the metal ring 33e that is positioned inside the lower large aperture 33b of the U-D angle knob 33, a second annular sealing member S3b which seals a gap between the axially-movable lock member 56 and the axially-immovable lock member 58, and a third annular sealing member S3c which seals a gap between the axially-movable lock member 56 and the cylindrical base 50.

As can be understood from the above descriptions, in a state where the steering device 13 is in an assembled condition, the L-R angle knob 23, the U-D angle knob 33 and the L-R lock knob 42 are each sealed in a watertight fashion so that fluid does not enter into the inner spaces 23i, 33i and 42i, respectively. However, the L-R angle knob 23, the U-D angle knob 33 and the L-R lock knob 42 are structured to allow gas to enter into the inner spaces 23i, 33i and 42i, respectively, when the endoscope 10 is sterilized with gas.

The endoscope 10 is provided in the housing 11a with an inner space 11i, which is positioned immediately below the substrate 11b as viewed in FIG. 2. As described above, the rotational shaft 20 extends upwards as viewed in FIG. 2 through the through hole 11c formed on the housing 11a. The annular gap between the stationary hollow cylindrical base 50 and the through hole 11c is sealed with the first sealing member group S1 and the covering member 11d. The first sealing member group S1 includes a first sealing member S1a which seals a gap between the housing 11a and the covering member 11d, and a second sealing member S1b which seals a gap between the covering member 11d and the cylindrical base 50. The volume of the inner space 11i is greater than the volume of each of the inner spaces 23i, 33i and 42i of the L-R angle knob 23, the U-D angle knob 33 and the L-R lock knob 42, respectively.

The inner end (lower end as viewed in FIG. 2) of the rotational shaft 20 is fixed to the substrate 11b positioned in the housing 11a, while the other end (upper end as viewed in FIG. 2) of the rotational shaft 20 is positioned in the inner space 42i of the L-R lock knob 42. The rotational shaft 20 is formed as a hollow shaft to be provided with an axial path (air passage) 20b extending between the opposite ends of the rotational shaft 20. The set screw 20a, which is screwed into the upper end of the rotational shaft 20, is formed to have an axial path 20z which connects the axial path 20b of the rotational shaft 20 with the inner space 42i of the L-R lock knob 42. The inner end of the axial path 20b of the rotational shaft 20 has a communicative connection with the inner space 11i of the housing 11a. Therefore, the inner space 42i of the L-R lock knob 42 and the inner space 11i of the housing 11a have a communicative connection with each other via the axial paths 20b and 20z.

The rotational shaft 20 is provided between the opposite ends thereof with four upper radial paths (air passage) 20c and two lower radial paths (air passage/first radial path) 20d. Each upper radial path 20c extends in a radial direction from the axial path 20b to the outer peripheral surface of the rotational shaft 20. Likewise, each lower radial path 20d extends in a radial direction from the axial path 20b to the outer peripheral surface of the rotational shaft 20.

The axial path 20b has a communicative connection with the inner space 23i of the L-R angle knob 23 via the upper radial paths 20c. Since the axial paths 20b has a communicative connection with the inner space 11i of the housing 11a, the inner space 23i of the L-R angle knob 23 and the inner space 11i of the housing 11a have a communicative connection with each other via the axial path 20b and the upper radial paths 20c. The four upper radial paths 20c are arranged at equi-angular intervals about the axis of the rotational shaft 20. Only three of the four upper radial paths 20c are shown in each of FIGS. 2, 3, 4 and 12. Likewise, the four lower radial paths 20d are arranged at equi-angular intervals about the axis of the rotational shaft 20. Only two of the four lower radial paths 20d are shown in each of FIGS. 2, 3, 4 and 12.

The outer end of each lower radial path 20d is covered by the cylindrical shaft portion 21a of the inner control shaft 21, the cylindrical shaft portion 31a of the outer control shaft 31 and the cylindrical base 50, in that order from the axial path 20b in a radially outward direction (see FIG. 2). An inner annular gap (air passage) 63a is formed between an outer peripheral surface of the rotational shaft 20 and an inner peripheral surface of the cylindrical shaft portion 21a of the inner control shaft 21 (see FIG. 13). A middle annular gap (air passage) 63b is formed between an outer peripheral surface of the inner control shaft 21 and an inner peripheral surface of the outer control shaft 31a (see FIG. 13). An outer annular gap (air passage) 63c is formed between an outer peripheral surface of the outer control shaft 31a and an inner peripheral surface of the stationary hollow cylindrical base 50 (see FIG. 13). The cylindrical shaft portion 21a of the inner control shaft 21 is provided with two inner radial through holes (air passage/second radial path) 64 via which the inner annular gap 63a and the middle annular gap 63b have a communicative connection with each other. The outer control shaft 31a is provided with two middle radial through holes (air passage/second radial path) 65 via which the middle annular gap 63b and the outer annular gap 63c have a communicative connection with each other. The cylindrical base 50 is provided with two outer annular gaps (air passage/second radial path) 66 via which the outer annular gap 63c and the inner space 33i of the U-D angle knob 33 have a communicative connection with each other.

Each lower radial path 20d has a communicative connection with the inner radial through hole 64 at all times via the inner annular gap 63a regardless of the relative rotational position between the cylindrical shaft portion 21a of the inner control shaft 21, which rotates together with the L-R angle knob 23, and the rotational shaft 20. Likewise, the inner radial through hole 64 has a communicative connection with the middle radial through hole 65 at all times via the middle annular gap 63b regardless of the relative rotational position between the cylindrical shaft portion 21a of the inner control shaft 21 and the cylindrical shaft portion 31a of the outer control shaft 31, which rotates together with the U-D angle knob 33. Likewise, the middle radial through hole 65 has a communicative connection with the outer radial through hole 66 at all times via the outer annular gap 63c regardless of the relative rotational position between the cylindrical shaft portion 31a of the outer control shaft 31 and the stationary hollow cylindrical base 50. Accordingly, each lower radial path 20d and the inner space 33i of the U-D angle knob 33 have a communicative connection with each other at all times. In other words, the inner annular gap 63a, the middle annular gap 63b and the outer annular gap 63c, the inner radial through hole 64, the middle radial through hole 65 and the outer radial through hole 66 together constitute a radial path, which is different from each lower radial path 20d, for making each lower radial path 20d and the inner space 33i communicate with each other at all times with the cylindrical shaft portion 21a, the cylindrical shaft portion 31a and the cylindrical base 50 being positioned between the rotational shaft 20 and the U-D angle knob 33.

Accordingly, in addition to the above described structure of making the inner space 42i of the L-R lock knob 42 have a communicative connection with the inner space 11i of the housing 11a, the inner space 33i of the U-D angle knob 33 has a communicative connection with the inner space 11i of the housing 11a via the axial path 20b, each lower radial path 20d, the inner radial through hole 64, the middle radial through hole 65, the outer radial through hole 66, the inner annular gap 63a, the middle annular gap 63b and the outer annular gap 63c.

As can be understood from the above description, in the first embodiment of the control device of the endoscope 10, the inner space 23i of the hollow L-R angle knob 23, the inner space 33i of the hollow U-D angle knob 33 and the inner space 42i of the hollow L-R lock knob 42 have a communicative connection with the inner space 11i of the housing 11a via the axial path 20b, the upper radial paths 20c and the lower radial paths 20d of the hollow rotational shaft 20, and other paths (axial path 20z, inner annular gap 63a, middle annular gap 63b, outer annular gap 63c, inner radial through hole 64, middle radial through hole 65 and outer radial through hole 66). The axial path 20b, the upper radial paths 20c, the lower radial paths 20d, the axial path 20z, the inner annular gap 63a, the middle annular gap 63b, the outer annular gap 63c, the inner radial through hole 64, the middle radial through hole 65 and the outer radial through hole 66 constitute a communicative connection device. With this structure, the internal pressure of the inner space 23i, the inner space 33i and the inner space 42i does not increase very much during the time the endoscope 10 is sterilized with gas since the internal pressure can escape from the inner space 23i, the inner space 33i and the inner space 42i to the inner space 11i of the housing 11a, the volume of which is greater than the volume of each of the inner spaces 23i, 33i and 42i, via the above described communicative connection device. This structure prevents the internal pressure of the inner space 23i, the inner space 33i and the inner space 42i from increasing excessively. Therefore, even if a large difference in pressure occurs between the outside and the inside of the endoscope 10, the elements of each of the L-R angle knob 23, the U-D angle knob 33 and the L-R lock knob 42 are not easily damaged. This makes it possible to reduce the wall thickness of each element of each of the L-R angle knob 23, the U-D angle knob 33 and the L-R lock knob 42. Furthermore, in the case where one or more of the L-R angle knob 23, the U-D angle knob 33 and the L-R lock knob 42 has an adhesive coated surface, the area of the adhesive coated surface can be made minimal.

The present invention is not limited solely to the particular embodiment described above. For instance, although the present invention is applied to the hollow L-R angle knob 23, the hollow U-D angle knob 33 and the hollow L-R lock knob 42 of the endoscope 10, the present invention can also be applied to a rotational control knob of any other instrument or apparatus which is used for other purposes.

In the first embodiment of the operational body 11 of the endoscope 10, although the rotational control knob (L-R lock knob 42) which is rotatably supported at an end of the hollow rotational shaft 20 is used to lock a steering knob (U-D angle knob 23), while each of the two rotational control knobs (U-D angle knob 23 and U-D angle knob 33) which is rotatably supported around the hollow rotational shaft 20 at a midpoint thereof between the opposite ends of the rotational shaft 20 is used to steer the bendable portion 12a, the supporting positions of these three rotational control knobs with respect to the rotational shaft 20 can be any other positions. Furthermore, the functions that these rotational control knobs have are not limited solely to the particular functions described above but can be any other functions. For instance, in the case where it is sufficient to provide the endoscope 10 with only one steering knob, this steering knob can be arranged at the position corresponding to the position of the L-R lock knob 42 so that no steering knob is supported around the rotational shaft 20 at any midpoints thereof between the opposite ends of the rotational shaft 20. In this case, the rotational shaft 20 only needs to be provided with the axial path 20b together with the axial path 20z of the set screw 20a, i.e., the rotational shaft 20 does not need to be provided with any of the radial paths 20c and 20d.

Furthermore, in the first embodiment of the operational body 11 of the endoscope 10, although the cylindrical shaft portion 21a of the inner control shaft 21 and the cylindrical base 50 (except for the cylindrical shaft portion 31a which rotates and supports the hollow U-D angle knob 33) are disposed between the inner space 33i of the hollow U-D angle knob 33 and the rotational shaft 20, only the cylindrical shaft portion 31a can be disposed between the inner space 33i and the rotational shaft 20 to simplify the structure of the gas passage which connects the axial path 20b and the inner space 33i.

FIGS. 14 through 24 show the second embodiment of the control device of the endoscope 10. Parts or elements which are substantially identical to those of the first embodiment of the control device of the endoscope 10 are designated by the same reference numerals.

Firstly, the L-R steering device 13LR of the second embodiment of the control device will be hereinafter discussed in detail. Only those parts or element of the L-R steering device 13LR which are different from those of the L-R steering device 13LR of the first embodiment will be hereinafter discussed. In the second embodiment of the control device of the endoscope 10, the rotational shaft 20 is not formed as a hollow shaft, so that the rotational shaft 20 is not provided with the axial path 20b, the upper radial paths 20c and the lower radial path 20d unlike the rotational shaft 20 of the first embodiment. The set screw 20a is not provided with the axial path 20z unlike the set screw 20a of the first embodiment. Furthermore, the inner control shaft 21 and the outer control shaft 31 are not provided with the inner radial through hole 64 and the middle radial through hole 65 unlike the inner control shaft 21 and the outer control shaft 31 of the first embodiment, respectively, while the cylindrical base 50 is not provided with the outer annular gap 66 unlike the cylindrical base 50 of the first embodiment.

The disk portion 21b of the inner control shaft 21 is provided around the outer edge thereof with an outer cylindrical portion 21d which extends upward from the outer edge of the disk portion 21b. The outer cylindrical portion 21d is provided on an outer peripheral surface thereof with a male thread 21e.

Figure 14:
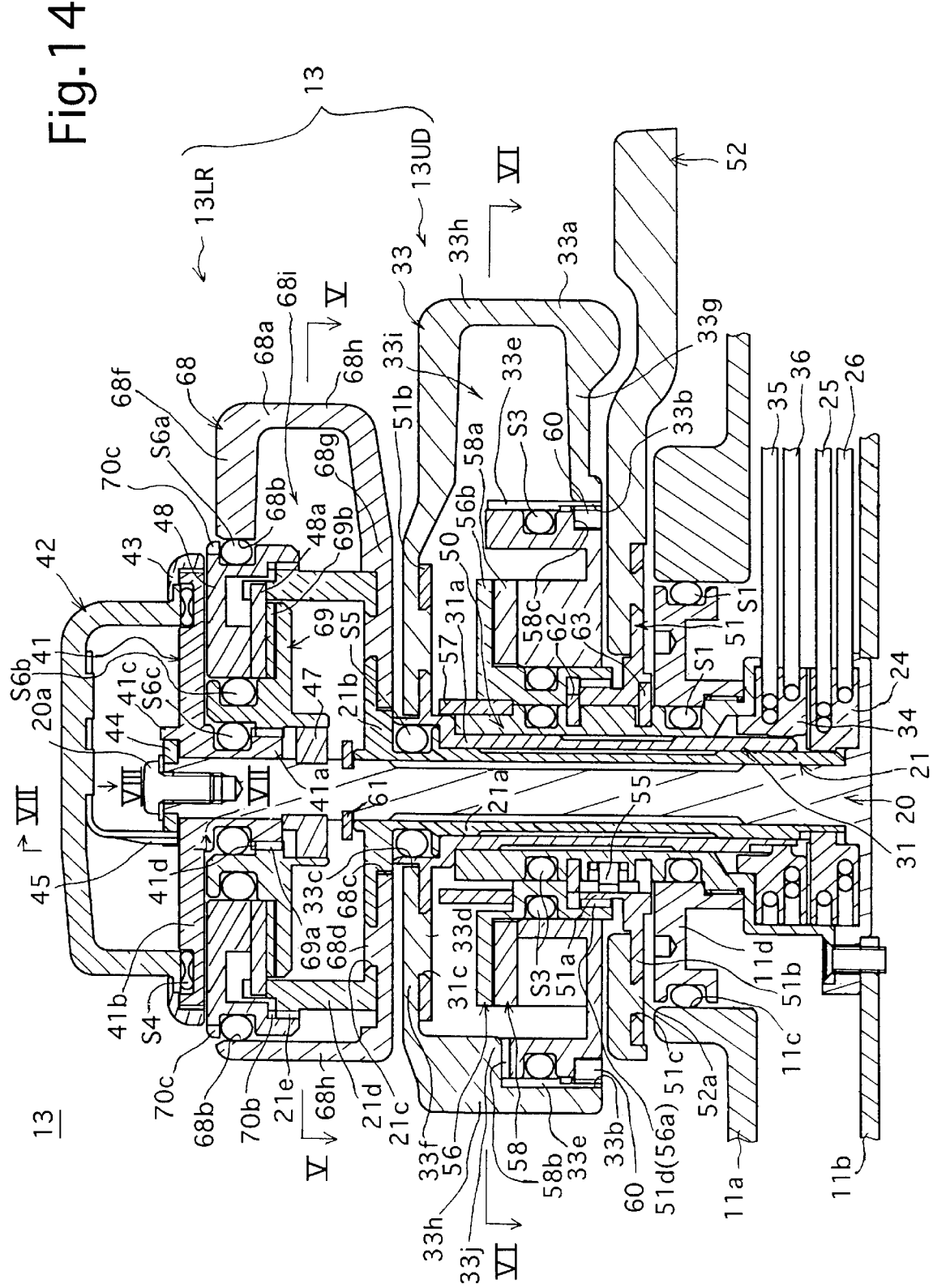
FIG. 14 is a view similar to FIG. 2 and illustrates fundamental elements of the second embodiment of the control device of the endoscope.
Figure 15:
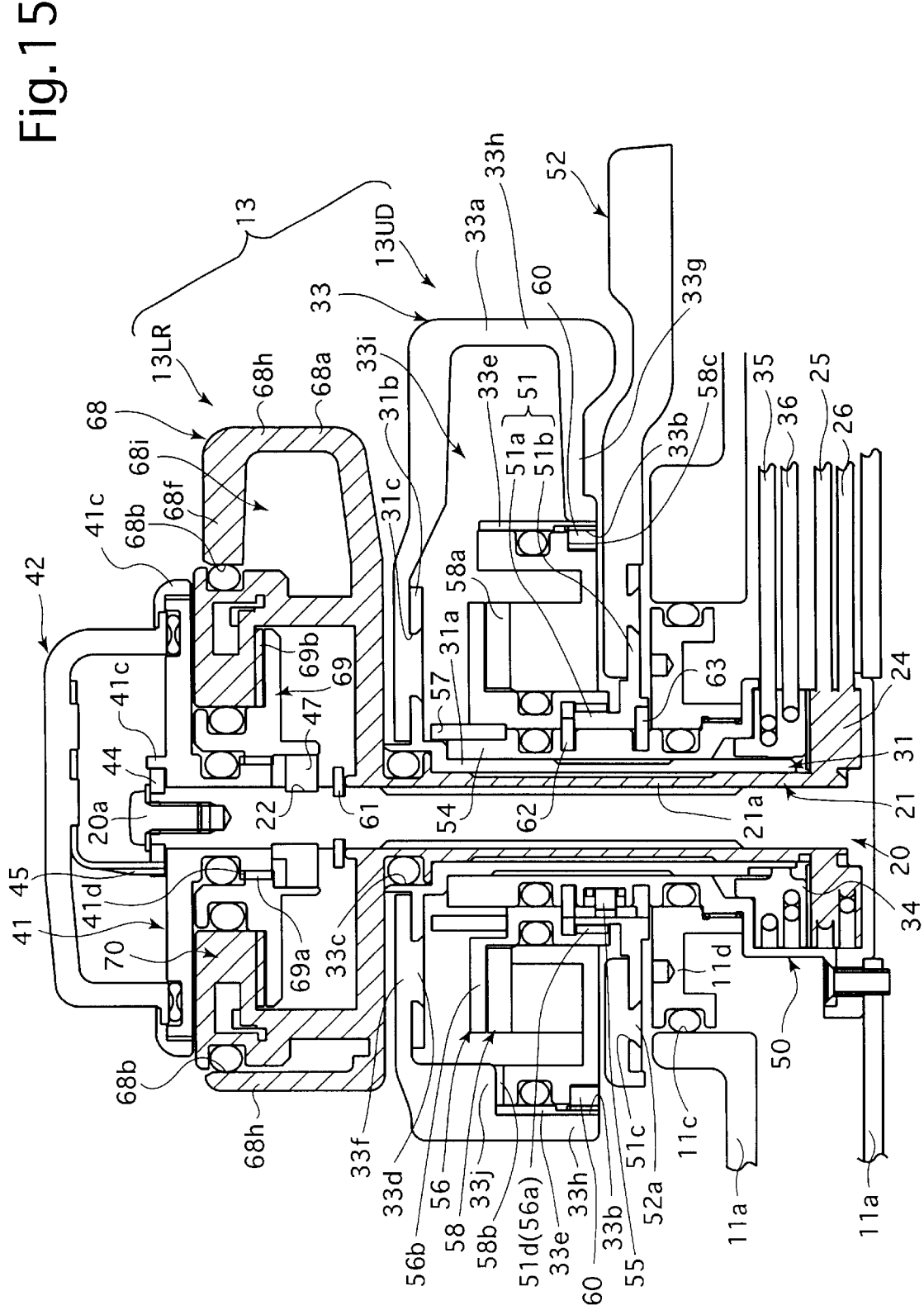
FIG. 15 is a view similar to FIG. 14 and illustrates elements of an L-R steering device which rotate together in the same rotational direction by the same angle of rotation as an integral element for the purpose of illustration.
Figure 16:
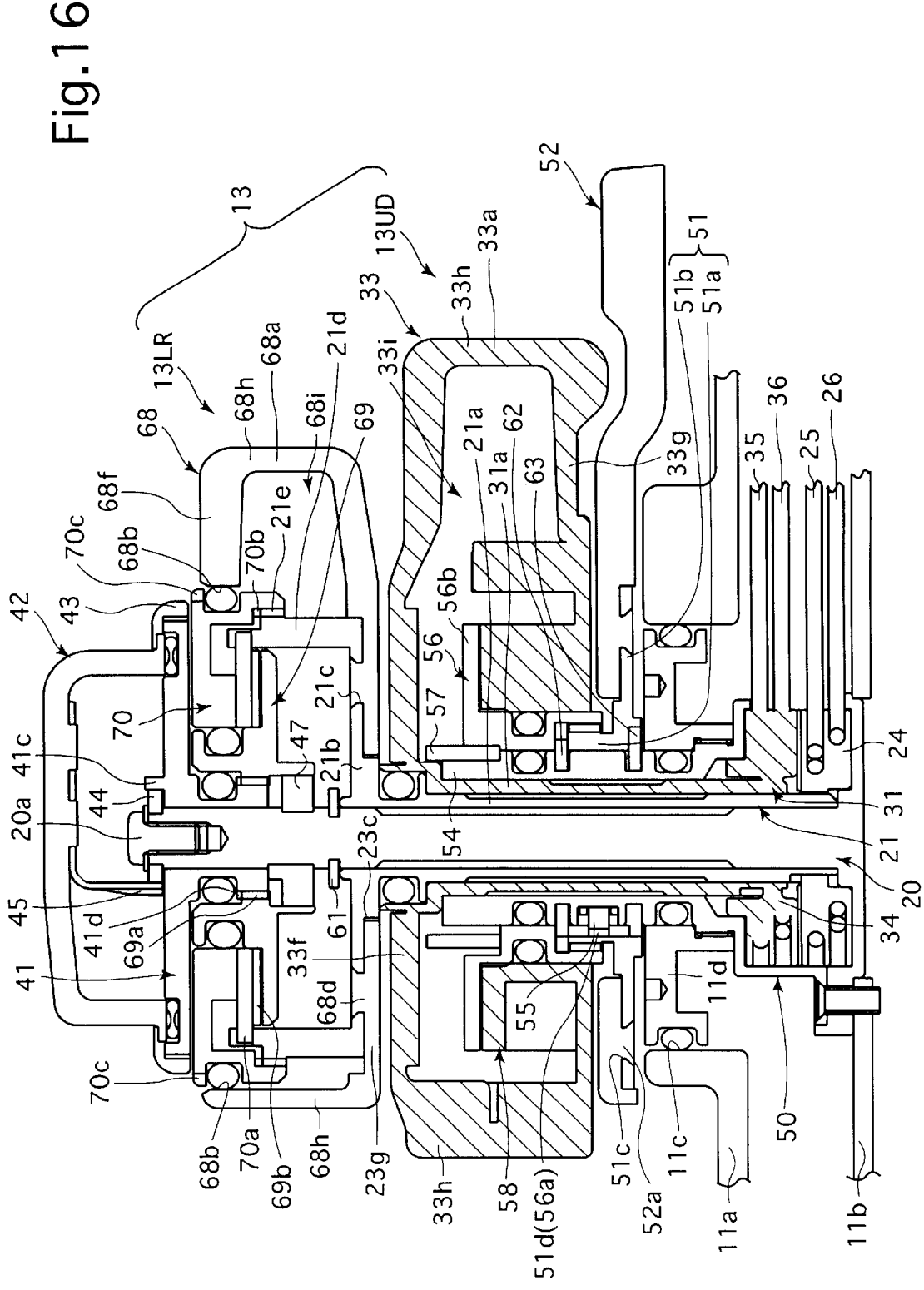
FIG. 16 is a view similar to FIG. 14 and illustrates elements of a U-D steering device which rotate together in the same rotational direction by the same angle of rotation as an integral element for the purpose of illustration.
Figure 17:
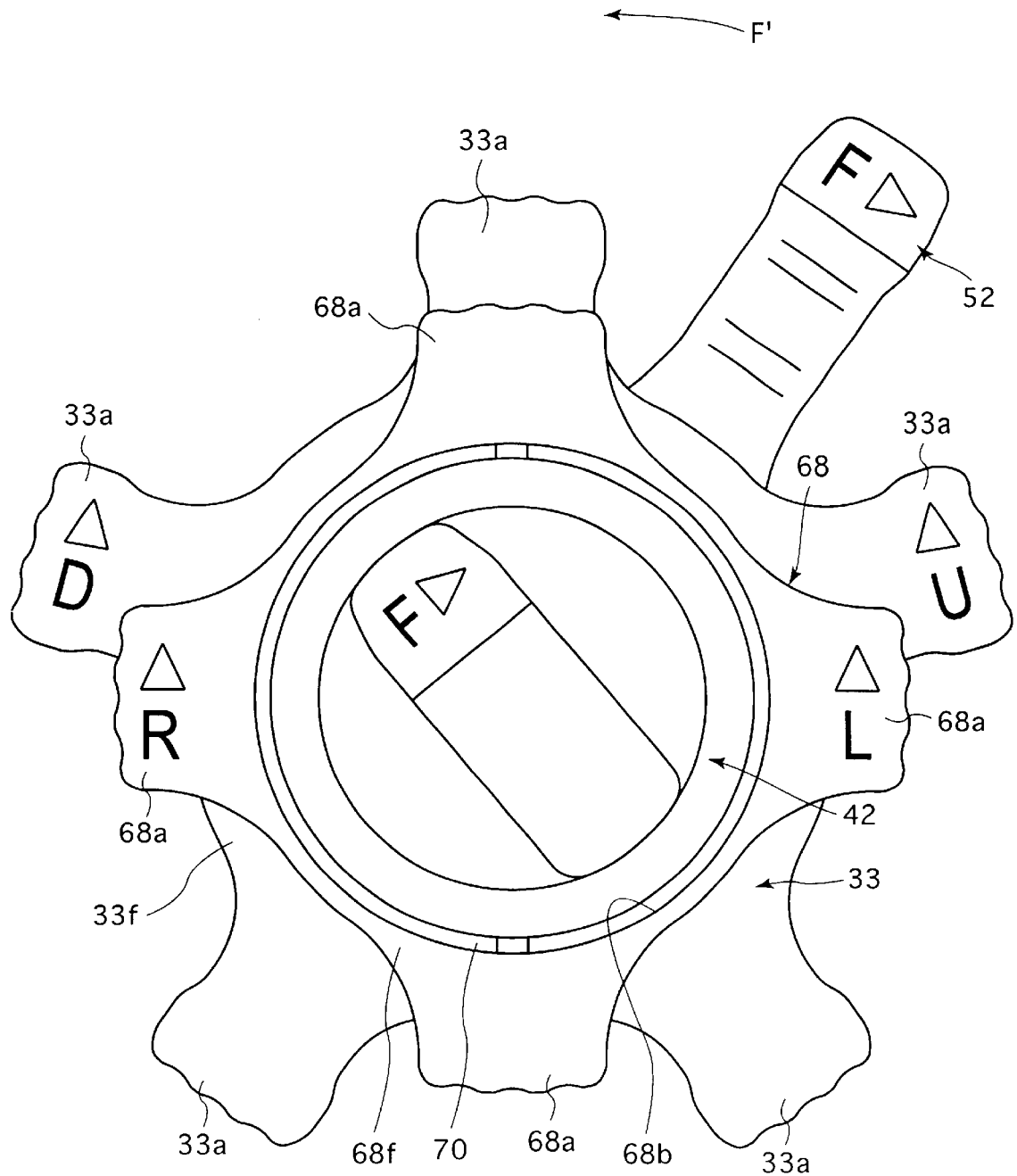
FIG. 17 is a plan view of the control device of the endoscope shown in FIG. 14.
Figure 18:
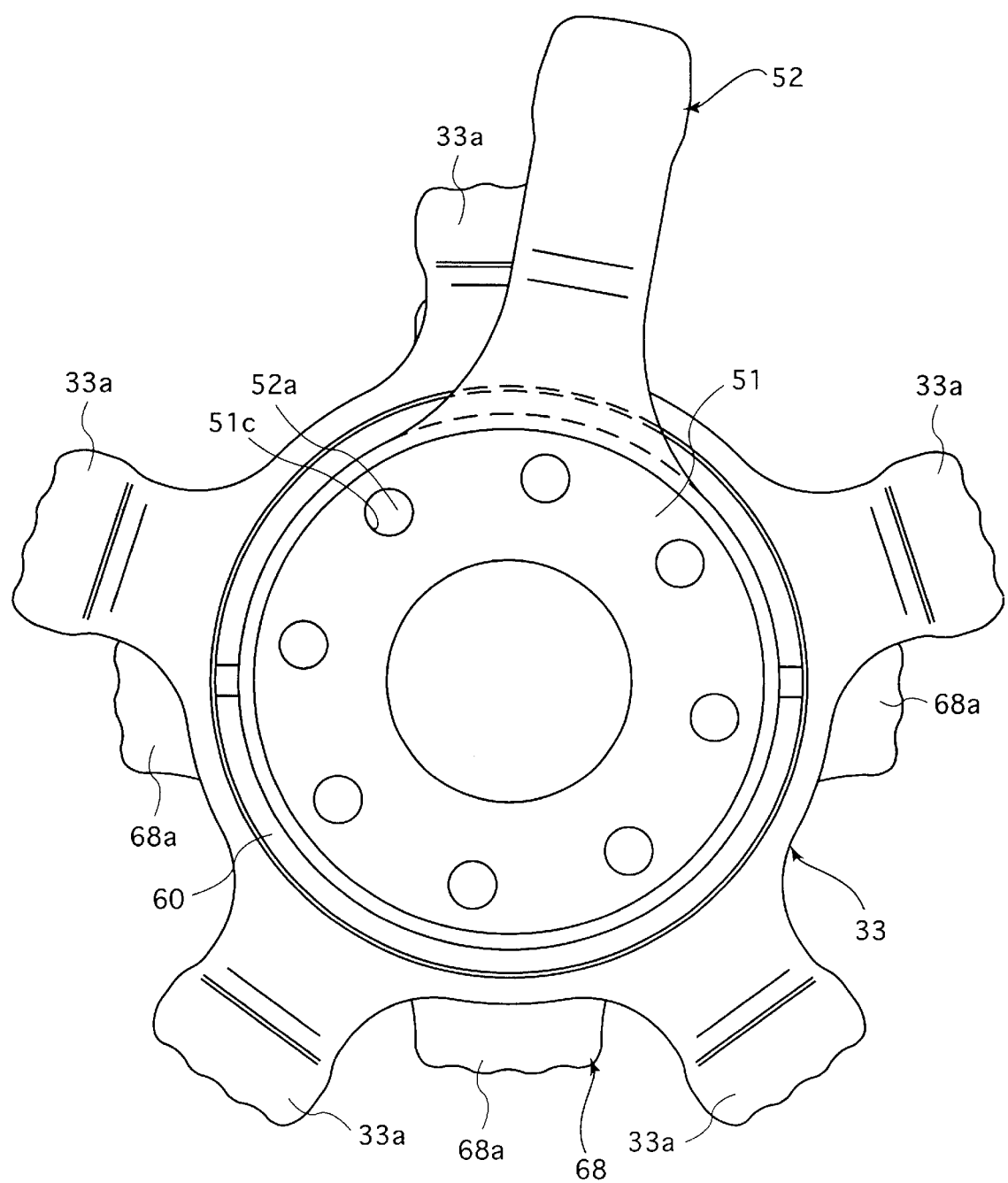
FIG. 18 is a bottom view of fundamental elements of the control device of the endoscope shown in FIG. 14.

The L-R steering device 13LR is provided with an L-R angle knob (L-R control knob) 68 that is made of plastic. The L-R angle knob 68 is fixed to the inner control shaft 21. As can be seen in FIG. 17, the L-R angle knob 68 is provided at equi-angular intervals with four hollow projecting portions 68a which extend radially outwards so that the operator can securely hold and turn the L-R angle knob 68 with his/her fingers engaging with the projecting portions 68a. The L-R angle knob 68 is formed as a hollow element as shown in FIGS. 14 through 16. The L-R angle knob 68 is provided on top and bottom portions thereof with an upper large circular aperture (opening) 68b and a lower small circular aperture 68c which have a large diameter and a small diameter, respectively. The disk portion 21b is fitted in the lower small aperture 68c. The L-R angle knob 68 is provided, on the bottom portion thereof in the vicinity of the lower small aperture 68c, with a plurality of projections 68d at equi-angular intervals about the axis of the rotational shaft 20. The plurality of projections 68d are firstly fitted in the plurality of circular holes 21c, respectively, and subsequently the tip of each projection 68d is melted by heat to fix the L-R angle knob 68 to the inner control shaft 21.

The L-R angle knob 68 of the L-R steering device 13LR is locked with a locking device to fix the bendable portion 12a to a desired curved shape in left or right direction, i.e., to fix the orientation of the tip of the bendable portion 12a in left or right direction. In the following description, the locking device for the L-R steering device 13LR in the second embodiment of the control device of the endoscope 10 will be hereinafter discussed in detail. Only those parts or element of the locking device for the L-R steering device 13LR which are different from those of the locking device for the L-R steering device 13LR of the first embodiment will be hereinafter discussed.

The cylindrical portion 41a of the first rotating member 41 is provided on an outer peripheral surface thereof with a male thread 41d. The locking device for the L-R steering device 13LR is provided inside the L-R angle knob 68 with an axially-movable lock member 69. The axially-movable lock member 69 is positioned around the rotational shaft 20 and is provided on an inner peripheral surface thereof with a female thread 69a which is in mesh with the male thread 41d of the cylindrical portion 41a. Similar to the first embodiment of the control device, the rotational shaft 20 is partly formed as a non-cylindrical portion 22 having a non-circular cross section. A (removable) retaining member 47 having a generally hexagonal section is fitted on the non-cylindrical portion 22 at the bottom of the axially-movable lock member 69, and is coupled to the axially-movable lock member 69 in a non-rotatable manner relative to the axially-movable lock member 69 to prevent the axially-movable lock member 69 from rotating relative to the rotational shaft 20. Thus, the axially-movable lock member 69 rotates together with the rotational shaft 20. Accordingly, turning the L-R lock knob 42 causes the axially-movable lock member 69 to move along the axis of the rotational shaft 20 without rotating about the rotational shaft 20 due to the engagement of the male thread 41d with the female thread 69a.

If the axially-movable lock member 69 moves up and down by rotation of the integral member including the first rotating member 41 and the L-R lock knob 42, a first friction pad 69b fixed to an upper face of the axially-movable lock member 69 is engaged with and disengaged from a second friction pad 70a fixed to an axially-immovable lock member (friction brake member) 70. Each of the first and second friction pads 69b and 70a is in the shape of a disk. The first friction pad 69b can be made of a material having a high coefficient of friction such as cork or silicone rubber, while the second friction pad 70a can be made of, for example, metal (e.g., stainless steel). The axially-immovable lock member 70 is coupled to the inner control shaft 21 via a female thread 70b which is formed on an inner peripheral surface of the axially-immovable lock member 70 and the aforementioned male thread 21e that meshes with the female thread 70b, so that the axially-immovable lock member 70 rotates together with the inner control shaft 21 when the L-R angle knob 68 is turned. If the first friction pad 69b is brought into pressing contact with the second friction pad 70a by an upward movement of the axially-movable lock member 69, the rotation of the axially-immovable lock member 70 is restricted by friction generated between the first and second friction pads 69b and 70a. If the axially-immovable lock member 70 is locked via the first and second friction pads 69b and 70a, the integral member including the inner control shaft 21 and the L-R angle knob 68 is prohibited from rotating, so that the first pulley 24 is also prohibited from rotating. As a result, the bendable portion 12a is prohibited from bending right and left, so that the bendable portion 12a can be locked to a desired curved shape in a left or right direction. More specifically, turning the L-R lock knob 42 in the direction of an arrow F' or a locking force applying direction (i.e., counterclockwise as viewed in FIG. 17) causes the axially-movable lock member 69 to move upward to bring the first friction pad 69b into pressing contact with the second friction pad 70a to thereby restrict the rotation of the L-R angle knob 68. On the other hand, turning the L-R lock knob 42 in the direction shown by a triangular arrow "Δ" and a letter "F" which are printed on the L-R lock knob 42 or a locking force releasing direction (i.e., clockwise as viewed in FIG. 17) causes the axially-movable lock member 69 to move downward to disengage the first friction pad 69b from the second friction pad 70a to thereby allow the L-R angle knob 68 to be turned freely. Although the L-R lock knob 42 stops with a click at each of the two stop positions thereof as has been described, the L-R angle knob 68 is locked when the L-R lock knob 42 stops at one of the two stop positions, while the L-R angle knob 68 is allowed to be turned when the L-R lock knob 42 stops at the other stop position. The former and latter stop positions are herein referred to as "lock position" and "unlock position", respectively. Each of the axially-movable lock member 69 and the axially-immovable lock member 70 is formed as an annular member so that the first friction pad 69b can be pressed against the second friction pad 70a regardless of the rotational position of the axially-immovable lock member 70, which rotates together with the L-R angle knob 68, relative to the axially-movable lock member 69.

In a state where the integral member including the inner control shaft 21 and the L-R angle knob 68 is prohibited from rotating, only the axially-immovable lock member 70 can be rotated relative to the outer cylindrical portion 21d to adjust the vertical position (i.e., the vertical position as viewed in FIG. 14) of the axially-immovable lock member 70 relative to the axially-movable lock member 69 via the engagement of the female thread 70b with the male thread 21e. If the vertical position of the axially-immovable lock member 70 relative to the axially-movable lock member 69 can be adjusted, the locking force applied to the L-R angle knob 68 can be adjusted since the frictional resistance between the first and second friction pads 69b and 70a in a state where the L-R lock knob 42 stops at the lock position varies. For instance, the frictional resistance between the first and second friction pads 69b and 70a can be set so that the bendable portion 12a is half-locked, i.e., so that the bendable portion 12a in a locked state is unlocked in accordance with the degree of an external force applied to the bendable portion 12a. Such an adjustment of the frictional resistance between the first and second friction pads 69b and 70a can be easily carried out by adjusting the vertical position of the axially-immovable lock member 70 by rotating the axially-immovable lock member 70 relative to the outer cylindrical portion 21d.

A sealing member group S6 includes a first sealing member S6a which seals a gap between an outer peripheral face of the axially-immovable lock member 70 and an inner peripheral face of the L-R angle knob 68, a second sealing member S6b which seals a gap between the axially-immovable lock member 70 and the axially-movable lock member 69, and a third sealing member S6c which seals a gap between the axially-movable lock member 69 and the first rotating member 41.

The L-R angle knob 68 is a bottomed hollow substantially cylindrical member having an inner space 68i which includes upper and lower walls 68f and 68g and a connecting wall (outer peripheral wall) 68h. The upper and lower walls 68f and 68g extend substantially perpendicular to the axis of the rotational shaft 20, while the connecting wall 68h extends substantially parallel to the axis of the rotational shaft 20 to connect the upper wall 68f with the lower wall 68g.

The lower wall 68g is provided with the aforementioned small aperture 68c having the center coaxial to the axis of the rotational shaft 20. The disk portion 21b of the inner control shaft 21 is fitted in the small aperture 68c to close the same. More specifically, the plurality of projections 68d are fitted in the plurality of circular holes 21c, respectively, and the tip of each projection 68d is melted by heat to fix the L-R angle knob 68 to the inner control shaft 21 so that the disk portion 21b lies on an inner surface (upper surface as viewed in FIG. 14) of the lower wall 68g. The cylindrical shaft portion 21a of the inner control shaft 21 extends downwards from the lower small aperture 68c to be fitted on the rotational shaft 20. Namely, the L-R angle knob 68 is supported by the rotational shaft 20 in a rotatable fashion about the rotational shaft 20 via the inner control shaft 21 that is fixed to the lower wall 68g of the L-R angle knob 68 (see FIG. 15). The inner control shaft 21 is made of metal while the L-R angle knob 68 is made of a resin. Therefore, as described above, when the inner control shaft 21 and the L-R angle knob 68 are fixed to each other, the tip of each projection 68d is melted by heat to fix the L-R angle knob 68 to the inner control shaft 21.

The upper large circular aperture 68b formed on the upper wall 68f of the L-R angle knob 68 provides a communicative connection between the inner space 68i of the L-R angle knob 68 and the outside of the L-R angle knob 68. The L-R angle knob 68 is provided at equi-angular intervals with four projecting portions 68a which extend radially outwards so that the operator can securely hold and turn the L-R angle knob 68 with his/her fingers engaging with the projecting portions 68a. The four projecting portions 68a are formed to extend radially outwards from the upper large aperture 68b. Through the upper large aperture 68b, molds (mold pieces) for forming the inner surface of the L-R angle knob 68 can be taken out of the inner space 68i of the L-R angle knob 68 after the L-R angle knob 68 is cast.

An assembly of fundamental elements (e.g., the first rotating member 41, the axially-immovable lock member 70 and the axially-movable lock member 69) of the locking device for the L-R angle knob 68 can be dismounted upward with respect to FIG. 14 from the cast L-R angle knob 68 via the large aperture 68b thereof. In the L-R steering device 13LR of the second embodiment, when the assembly is mounted to the L-R angle knob 68, the cylindrical portion 41a of the first rotating member 41, the axially-movable lock member 69 and the axially-immovable lock member 70 are positioned in the inner space 68i of the L-R angle knob 68. In this state, the outer diameter of the axially-immovable lock member 70, which is the outermost element among the cylindrical portion 41a, the axially-movable lock member 69 and the axially-immovable lock member 70 in a radial direction about the rotational shaft 20, is slightly smaller than the inner diameter of the upper large aperture 68b. On the other hand, the inner diameter of the cylindrical portion 41a, which is the innermost element among the cylindrical portion 41a, the axially-movable lock member 69 and the axially-immovable lock member 70 in the same radial direction about the rotational shaft 20, is slightly greater than the diameter of the rotational shaft 20 so that the cylindrical portion 41a can be fitted on the rotational shaft 20. Similar to the axially-immovable lock member 70, the axially-movable lock member 69, which is an annular member whose center is coaxial to the axis of the rotational shaft 20, is positioned between the axially-immovable lock member 70 and the cylindrical portion 41a of the first rotating member 41 in the same radial direction about the rotational shaft 20. Due to this structure, the assembly of fundamental elements of the locking device for the L-R angle knob 68 can be mounted to and dismounted from the L-R angle knob 68 via the upper large aperture 68b without disassembling the L-R angle knob 68.

The L-R steering device 13LR of the second embodiment is characterized in that the L-R angle knob 68 is formed as a hollow casting made of a resin which includes the aforementioned upper and lower walls 68f and 68g and the connecting wall 68h which connects the upper wall 68f with the lower wall 68g. A method of molding the L-R angle knob 68 will be hereinafter discussed with reference to FIGS. 19 through 24.

The L-R angle knob 68 is an injection molded casting which is cast with a mold 80 having seven mold pieces (81 through 87). The mold 80 is provided with a lower mold piece (first mold piece group) 81 which has an inner surface 81a for forming the outer surface of the lower wall 68g and an inner surface 81b for forming a half (lower half) of the outer surface of the connecting wall 68h. The mold 80 is provided with an upper mold piece (first mold piece group) 82 which is used in combination with the lower mold piece 81. The upper mold piece 82 has an inner surface 82a for forming the outer surface of the upper wall 68f and an inner surface 82b for forming another half (upper half) of the outer surface of the connecting wall 68h. The lower and upper mold pieces 81 and 82 are provided with positioning surfaces 81c and 82c, respectively, for registration of the lower and upper mold pieces 81 and 82.

The upper mold piece 82 is provided with a through hole 82d having a diameter slightly greater than the diameter of the upper large circular aperture 68b of the L-R angle knob 68. The mold 80 is further provided with a center mold piece (third mold piece group) 83 and four peripheral mold pieces (second mold piece group) 84, 85, 86 and 87. The center mold piece 83 and the four peripheral mold pieces 84, 85, 86 and 87 can be inserted into and taken out of the through hole 82d. The center mold piece 83 is formed as a cylinder having a cross section which allows the center mold piece 83 to be inserted into and taken out of the through hole 82d. The center mold piece 83 is provided with four surfaces 83a each of which is used for forming a corresponding part of the inner face of the connecting wall 68h (see FIG. 23). The center mold piece 83 is provided at the bottom face thereof with a center circular projection 83b for forming the small circular aperture 68c, and a plurality of circular recesses 83c for respectively forming the plurality of projections 68d.

Figure 23:
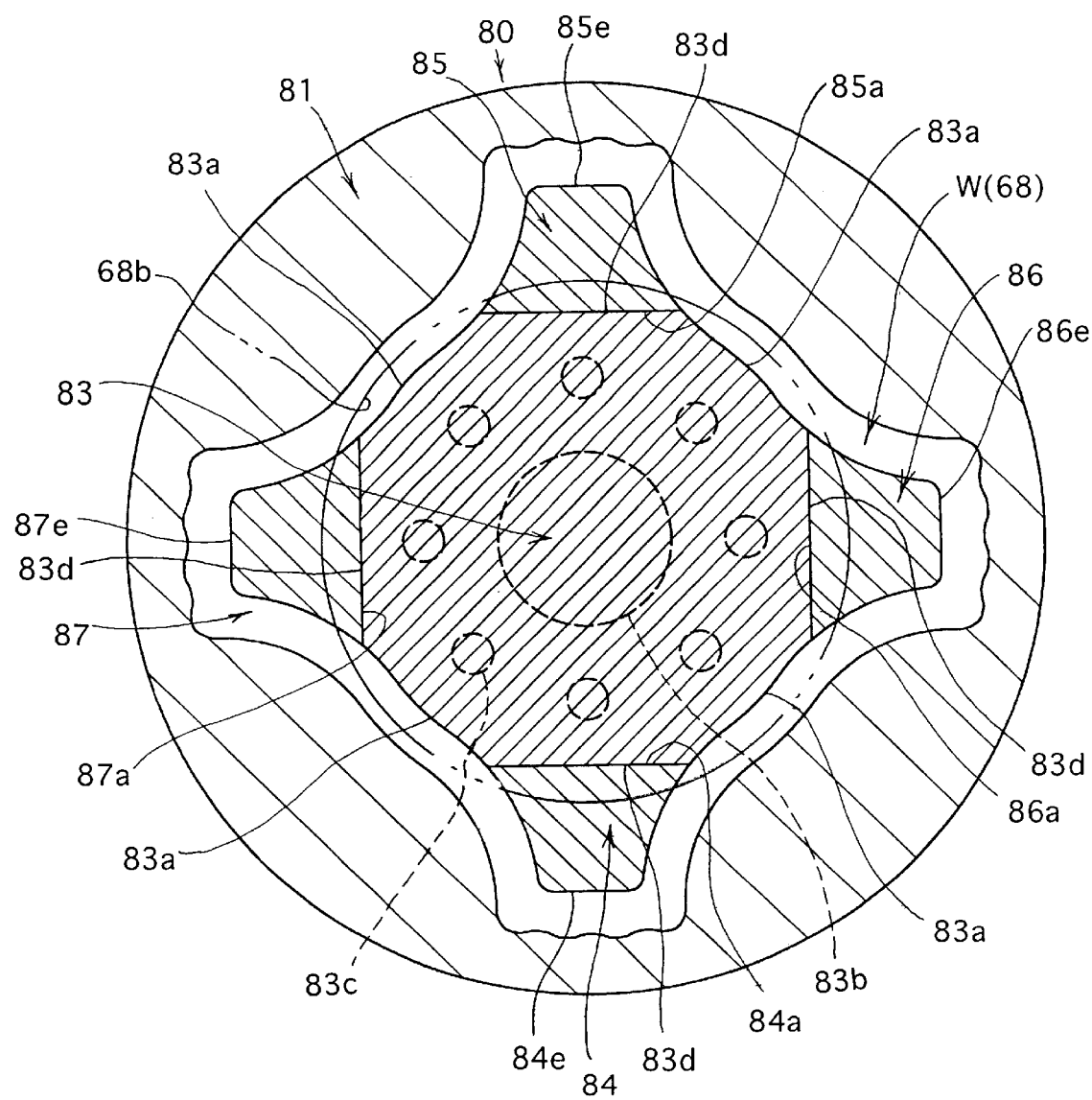
FIG. 23 is a cross sectional view of the mold shown in FIG. 19, taken along XXIII—XXIII line in FIG. 19, viewed in the direction of the appended arrows.

The four peripheral mold pieces 84, 85, 86 and 87 are arranged at equi-angular intervals (at intervals of 90 degrees) about the center circular projection 83b, and are used to form inner surfaces of the four projecting portions 68a, respectively (see FIG. 23). The peripheral mold piece 84 is provided with an inner positioning surface 84a which comes in contact with a positioning surface 83d of the center mold piece 83, an outer positioning surface 84b which comes in contact with part of an inner annular surface of the upper mold piece 82 which defines the through hole 82d, a surface 84c for forming part of the inner surface of the lower wall 68g, a surface 84d for forming part of the inner surface of the upper wall 68f, and a surface 84e for forming part of the inner surface of the connecting wall 68h. The peripheral mold piece 85, which is positioned on the opposite side of the center mold piece 83 from the peripheral mold piece 84, has the same structure as the peripheral mold piece 84, so that the peripheral mold piece 85 is provided with an inner positioning surface 85a, an outer positioning surface 85b, a surface 85c, a surface 85d and a surface 85e which correspond to the inner positioning surface 84a, the outer positioning surface 84b, the surface 84c, the surface 84d and the surface 84e of the peripheral mold piece 84, respectively. The peripheral mold pieces 86 and 87 are arranged on opposite sides of the center mold piece 83 in a manner similar to the peripheral mold pieces 84 and 85. Similar to each of the peripheral mold pieces 84 and 85, the peripheral mold piece 86 is provided with an inner positioning surface 86a, an outer positioning surface 86b, a surface (not shown) corresponding to the surface 84c or 85c, a surface (not shown) corresponding to the surface 84d or 85d, and a surface 86e which corresponds to the inner positioning surface 84a or 85a. Likewise, the peripheral mold piece 87 is provided with an inner positioning surface 87a, an outer positioning surface 87b, a surface (not shown) corresponding to the surface 84c or 85c, a surface (not shown) corresponding to the surface 84d or 85d, and a surface 87e which corresponds to the inner positioning surface 84a or 85a.

Figure 19:
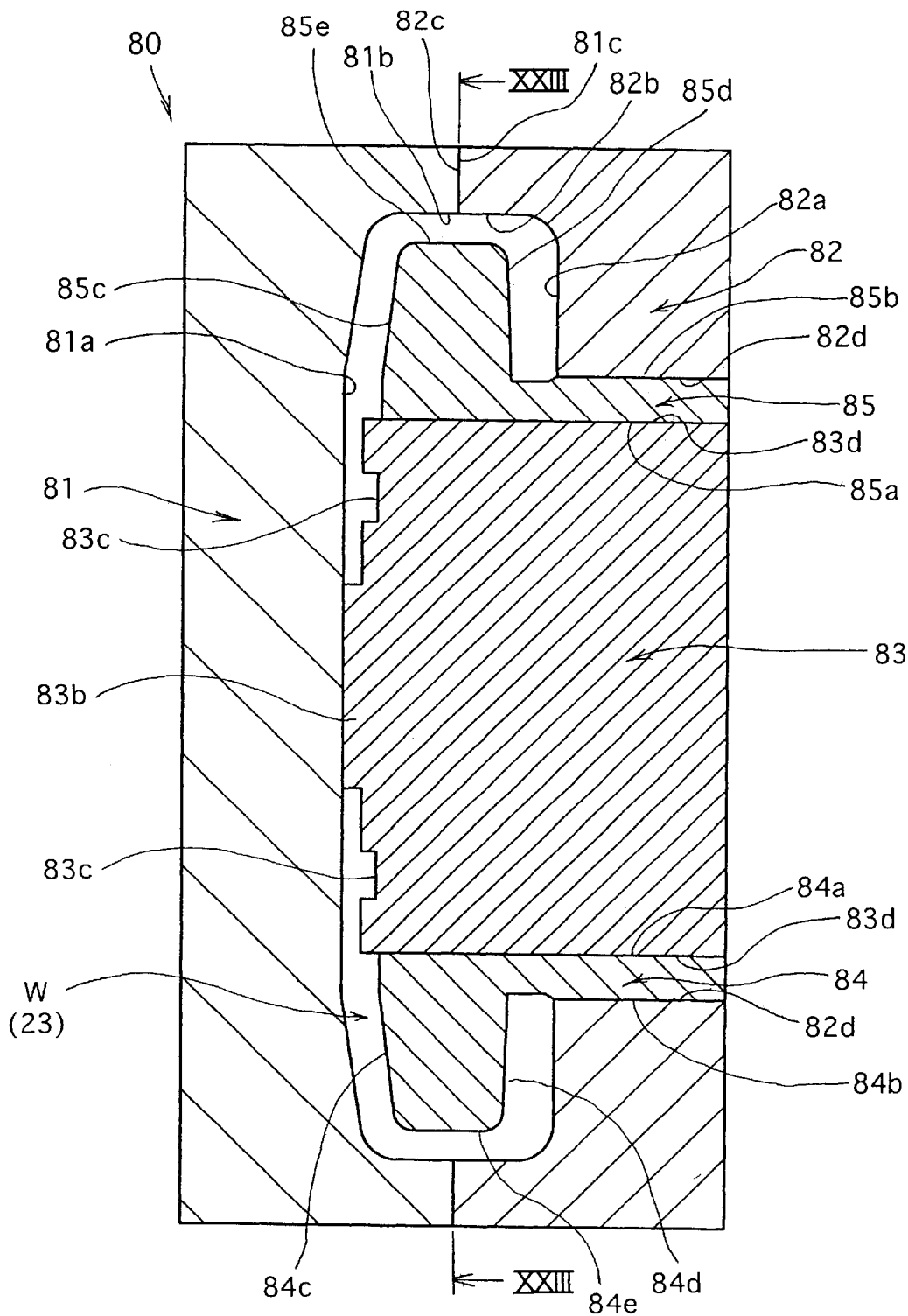
FIG. 19 is a cross sectional view of a mold for molding an L-R angle knob of the L-R steering device, explaining a method of molding the L-R angle knob.

FIGS. 19 and 23 show a state where the above described seven mold pieces 81 through 87 are combined together to form the mold 80. In this state, the shape of a cast space W which is formed by a combination of the seven mold pieces 81 through 87 corresponds to the shape of the L-R angle knob 68. Therefore, the L-R angle knob 68 is cast by injecting a molten casting resin into the cast space W and thereafter by cooling the injected casting resin.

Figure 20:
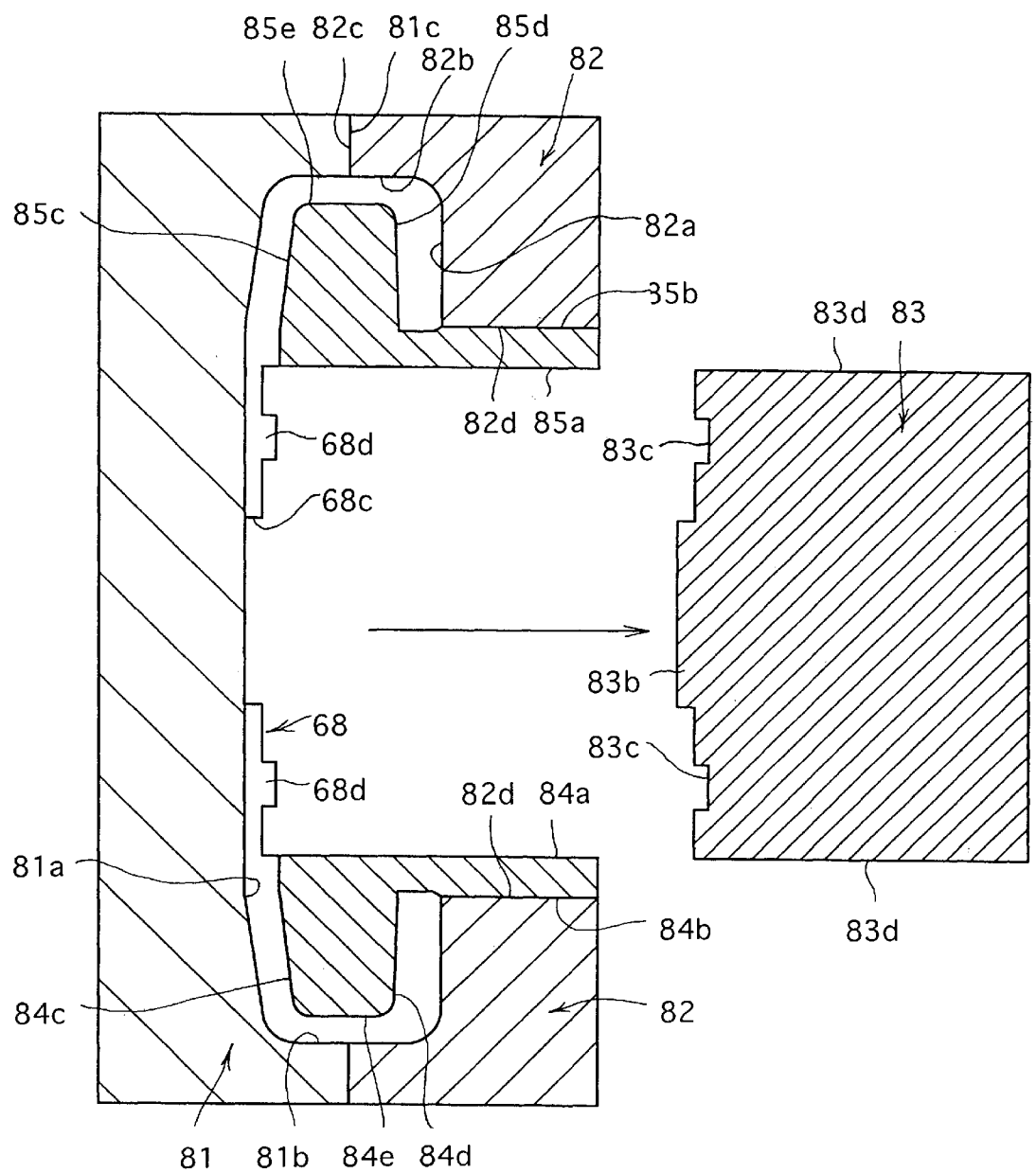
FIG. 20 is a cross sectional view of the mold shown in FIG. 19 in a different state, explaining the method of molding the L-R angle knob.
Figure 21:
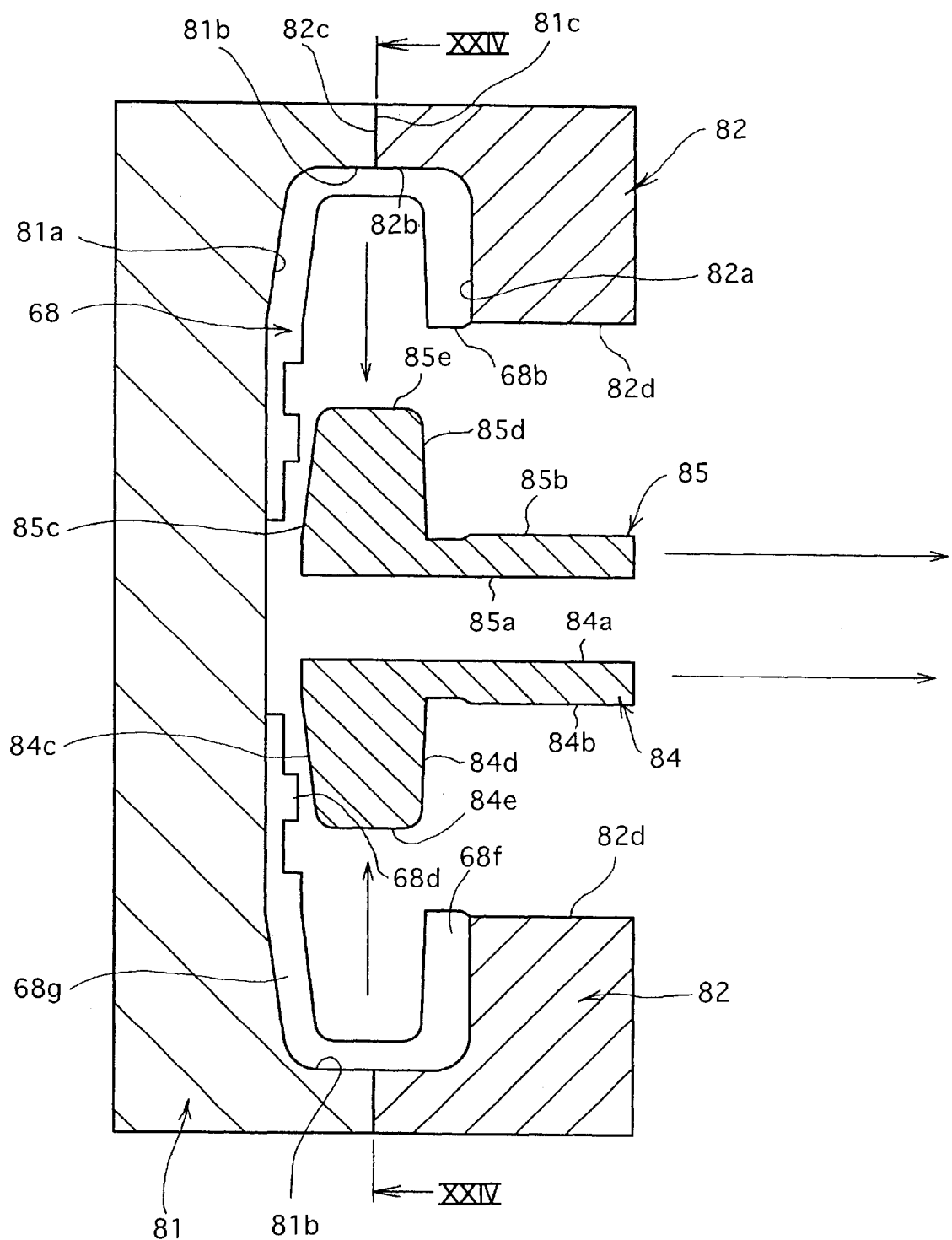
FIG. 21 is a cross sectional view of the mold shown in FIG. 19 in a different state, explaining the method of molding the L-R angle knob.
Figure 22:
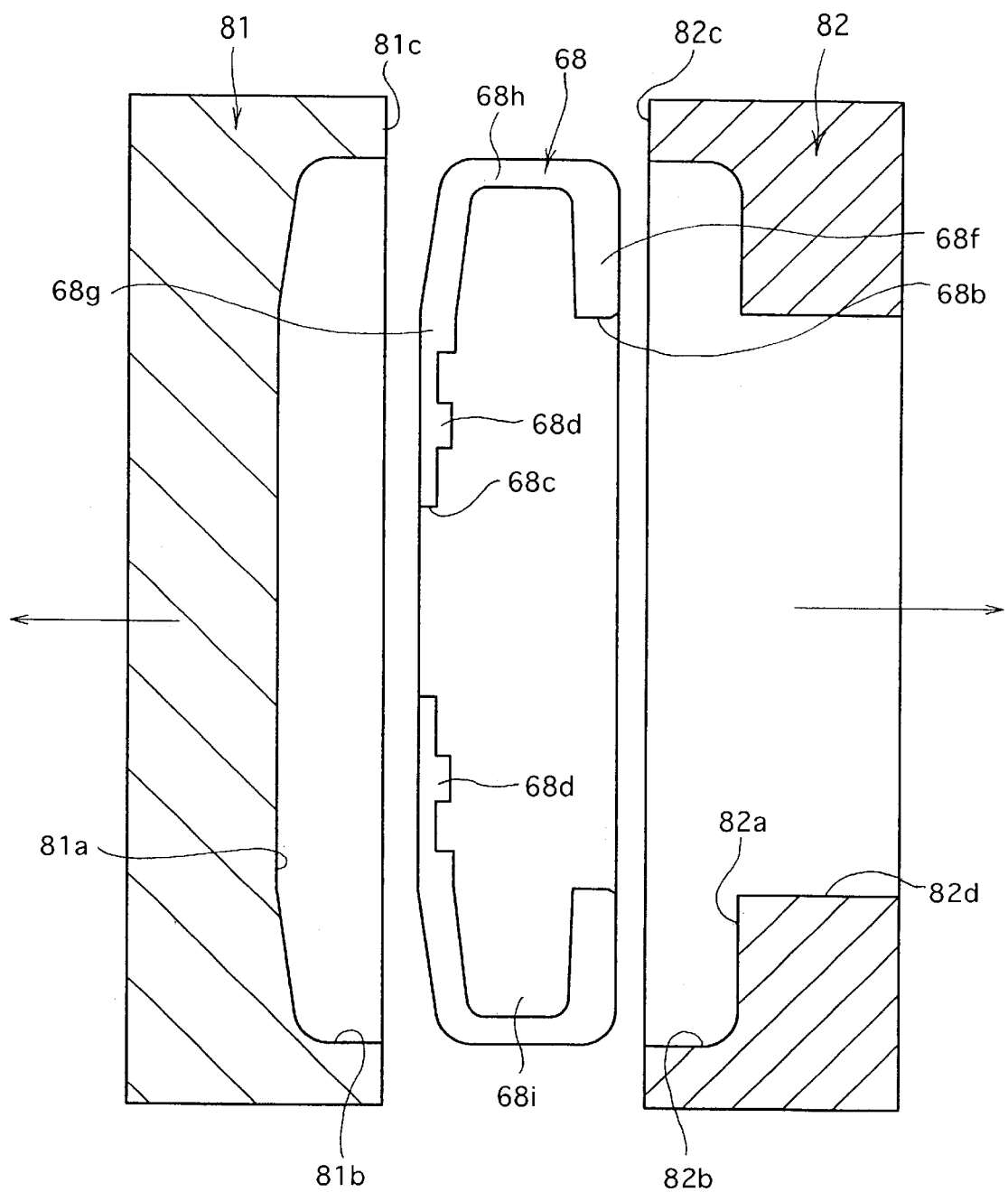
FIG. 22 is a cross sectional view of the mold shown in FIG. 19 in a different state, explaining the method of molding the L-R angle knob.
Figure 24:
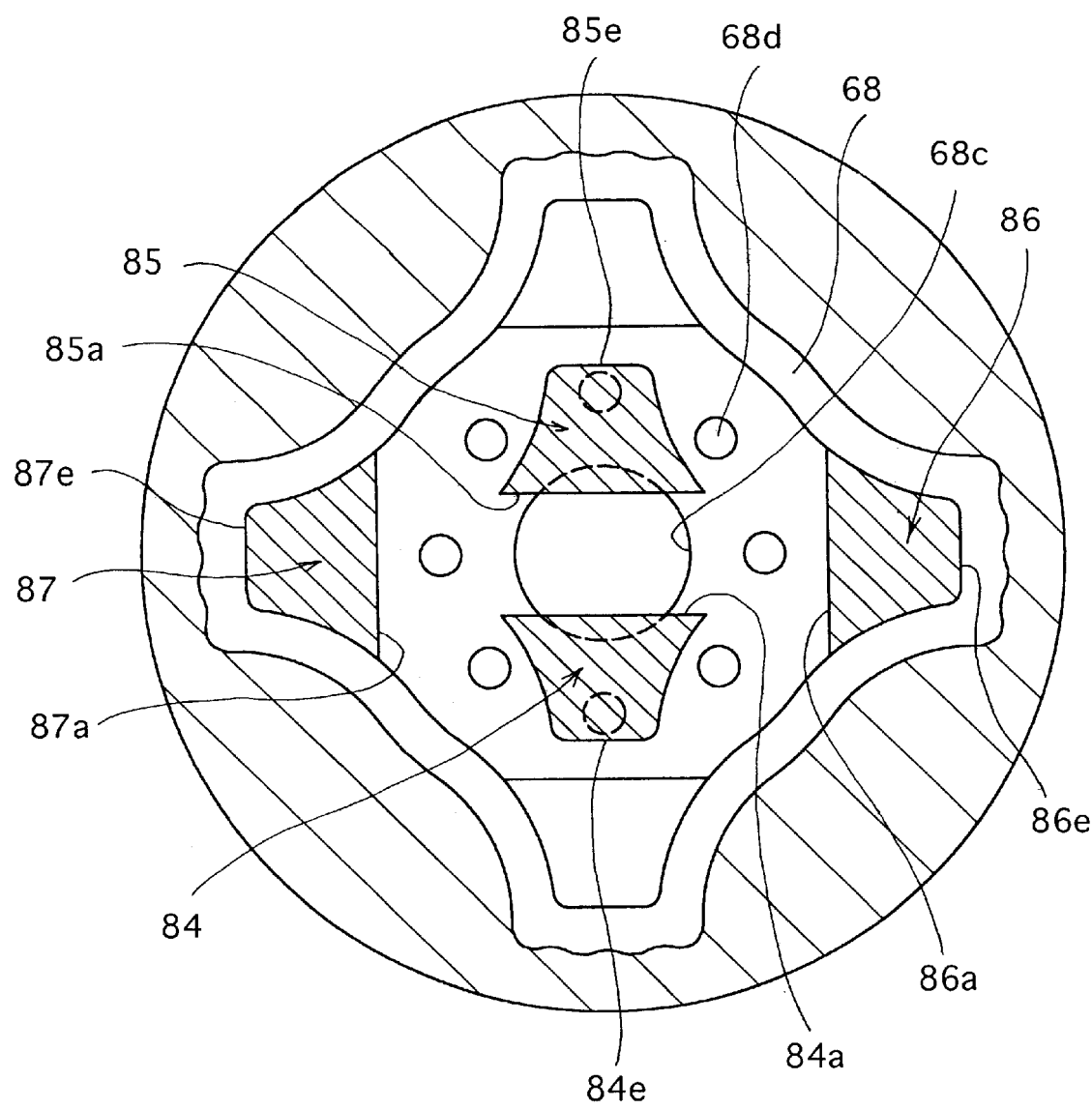
FIG. 24 is a cross sectional view of the mold shown in FIG. 19, taken along XXIV—XXIV line in FIG. 21, viewed in the direction of the appended arrows.

When the mold 80 is disassembled, firstly the center mold piece 83 is removed in a direction to be moved out of the large circular aperture 68b of the L-R angle knob 68 as shown in FIG. 20. Thereafter the four peripheral mold pieces 84, 85, 86 and 87 can be removed via the large circular aperture 68b (i.e., the through hole 82d of the upper mold piece 82). Thereafter, as shown in FIGS. 21 and 24, the peripheral mold pieces 84 and 85, which face each other after the center mold piece 83 is removed, are firstly moved in directions closely toward each other, and are subsequently removed via the large circular aperture 68b. Similarly, the peripheral mold pieces 86 and 87, which face each other after the center mold piece 83 is removed, are firstly moved in directions to be close to each other, and are subsequently removed via the large circular aperture 68b. Thereafter, the lower and upper mold pieces 81 and 82 are separated from each other as shown in FIG. 22. This completes the operation of molding the L-R angle knob 68.

In the above described molding method, although the mold pieces 83 through 87 are removed before the lower and upper mold pieces 81 and 82 are separated from each other, the mold pieces 83 through 87 can be removed after the lower and upper mold pieces 81 and 82 are separated from each other. Furthermore, the four peripheral mold pieces 84 through 87 can be removed in any order.

As can be understood from the above description, the L-R angle knob 68 is formed as a hollow member having a single-piece construction. This saves time as compared with the case where an angle knob whose shape is similar to the shape of the L-R angle knob 68 is made out of a plurality of external elements. Moreover, according to the L-R angle knob 68, such a plurality of external elements do not have to be assembled while ensuring the watertight construction of the angle knob. Accordingly, the L-R angle knob 68 can be made easily with a low cost of production. Furthermore, no mold seam is formed on the external surface of the L-R angle knob 68 (e.g., on the external surface of the connecting wall 68h), so that the external surface of the L-R angle knob 68 is quite smooth, which makes it easy to wash and clean the L-R angle knob 68.

Although the L-R angle knob 68 is supported by the rotational shaft 20 via the inner control shaft 21, the L-R angle knob 68 and the inner control shaft 21 are fixed to each other via the plurality of circular holes 21c, which are formed on the disk portion 21b of the inner control shaft 21, and the plurality of projections 68d, which are formed on the lower wall 68g of the L-R angle knob 68 to be respectively engaged in the plurality of circular holes 21c. Accordingly, the disk portion 21b is fixed to an inner surface (upper surface as viewed in FIG. 14) of the lower wall 68g. With this structure, the boundary between the L-R angle knob 68 and the inner control shaft 21 is not exposed to the outside of the L-R steering device 13LR very much, which makes it easy to wash and clean the L-R steering device 13LR.

In the L-R angle knob 68, the large circular aperture 68b which makes it possible to dismount the mold pieces 83 through 87 from the inside of the L-R angle knob 68 also makes it possible to dismount and mount the aforementioned assembly of fundamental elements of the locking device for the L-R angle knob 68 from and to the L-R angle knob 68. When the assembly of fundamental elements of the locking device for the L-R angle knob 68 is mounted to the L-R angle knob 68, the large circular aperture 68b is closed in a watertight fashion via the annular sealing members S6a, S6b and S6c of the assembly, and via the annular sealing member S4 which is positioned between the assembly and the L-R angle knob 68. Accordingly, the inner space 68i of the L-R angle knob 68 is maintained as a watertight space even though the large aperture 68b is formed on the L-R angle knob 68.

Similar to the L-R angle knob 68, the U-D angle knob 33 is an inverted bottomed hollow substantially cylindrical member having an inner space 33i which includes upper and lower walls 33f and 33g and a connecting wall (outer peripheral wall) 33h. The upper and lower walls 33f and 33g extend substantially perpendicular to the axis of the rotational shaft 20, while the connecting wall 33h extends substantially parallel to the axis of the rotational shaft 20 to connect the upper wall 33f with the lower wall 33g.

The upper wall 33f is provided with the aforementioned small aperture 33c having the center coaxial to the axis of the rotational shaft 20. The disk portion 31b of the outer control shaft 31 is fitted in the small aperture 33c to close the same. More specifically, the plurality of projections 33d are fitted in the plurality of circular holes 31c, respectively, and the tip of each projection 33d is melted by heat to fix the U-D angle knob 33 to the outer control shaft 31 so that the disk portion 31b lies on an inner surface (lower surface as viewed in FIG. 14) of the upper wall 33f. The cylindrical shaft portion 31a of the outer control shaft 31 extends downwards from the lower small aperture 33c to be fitted on the cylindrical shaft portion 21a of the inner control shaft 21. Namely, the U-D angle knob 33 is supported by the rotational shaft 20 in a rotatable fashion about the rotational shaft 20 via the outer control shaft 31 that is fixed to the upper wall 33f of the U-D angle knob 33 (see FIG. 14). The outer control shaft 31 is made of metal and the U-D angle knob 33 is made of a resin. Therefore, as described above, when the outer control shaft 31 and the U-D angle knob 33 are fixed to each other, the tip of each projection 33d is melted by heat to fix the U-D angle knob 33 to the outer control shaft 31.

The lower large circular aperture 33b formed on the lower wall 33g of the U-D angle knob 33 provides a communicative connection between the inner space 33i of the U-D angle knob 33 and the outside of the U-D angle knob 33. The U-D angle knob 33 is provided at equi-angular intervals with five hollow projecting portions 33a which extend radially outwards so that the operator can securely hold and turn the U-D angle knob 33 with his/her fingers engaging with the projecting portions 33a. The five projecting portions 33a are formed to extend radially outwards from the lower large aperture 33b. Similar to the upper large aperture 68b molds (mold pieces) for forming the inner surface of the U-D angle knob 33 can be taken out of the inner space 33i of the U-D angle knob 33 through the lower large aperture 33b after the U-D angle knob 33 is cast.

An assembly of fundamental elements (e.g., the second rotating member 51, the axially-immovable lock member 56 and the axially-movable lock member 58) of the locking device for the U-D angle knob 33 can be dismounted downward with respect to FIG. 14 from the cast U-D angle knob 33 via the large aperture 33b thereof. In the U-D steering device 13UD of the second embodiment, when the assembly is mounted to the U-D angle knob 33, the cylindrical portion 51a of the second rotating member 51, the axially-movable lock member 56 and the axially-immovable lock member 58 are positioned in the inner space 33i of the U-D angle knob 33. In this state, the outer diameter of the axially-immovable lock member 58, which is the outermost element among the cylindrical portion 51a, the axially-movable lock member 56 and the axially-immovable lock member 58 in a radial direction about the cylindrical base 50 and the rotational shaft 20, is slightly smaller than the inner diameter of the lower large aperture 33b. On the other hand, the inner diameter of the cylindrical portion 51a, which is the innermost element among the cylindrical portion 51a, the axially-movable lock member 56 and the axially-immovable lock member 58 in the same radial direction about the cylindrical base 50 and the rotational shaft 20, is slightly greater than the diameter of the cylindrical base 50 so that the cylindrical portion 51a can be fitted on the cylindrical base 50. Similar to the axially-immovable lock member 58, the axially-movable lock member 56, which is an annular member whose center is coaxial to the axis of the rotational shaft 20, is positioned between the axially-immovable lock member 58 and the cylindrical portion 51a of the second rotating member 51 in the same radial direction about the rotational shaft 20. Due to this structure, the assembly of fundamental elements of the locking device for the U-D angle knob 33 can be mounted to and dismounted from the U-D angle knob 33 via the lower large aperture 33b without disassembling the U-D angle knob 33.

Similar to the L-R angle knob 68, the U-D angle knob 33 is formed as a hollow casting made of a resin which includes the aforementioned upper and lower walls 33f and 33g and the connecting wall 33h which connects the upper wall 33f with the lower wall 33g. The U-D angle knob 33 is an injection molded casting which can be cast according to a method similar to the above described method of molding the L-R angle knob 68. Therefore, the description about a method of molding the U-D angle knob 33 is omitted.

The U-D angle knob 33 is formed as a hollow member having a single-piece construction, similar to the L-D angle knob 68. Such a construction saves time as compared with the case where an angle knob whose shape is similar to the shape of the U-D angle knob 33 is made out of a plurality of external elements. Moreover, according to the U-D angle knob 33, it is not necessary to assemble such a plurality of external elements while ensuring the watertight construction of the angle knob. Accordingly, the U-D angle knob 33 can be made easily at a low cost of production. Furthermore, no mold seam is formed on the external surface of the U-D angle knob 33 (e.g., on the external surface of the connecting wall 33h), so that the external surface of the U-D angle knob 33 is quite smooth, which makes it easy to wash and clean the U-D angle knob 33.

Although the U-D angle knob 33 is supported by the rotational shaft 20 via the outer control shaft 31, the U-D angle knob 33 and the outer control shaft 31 are fixed to each other via the plurality of circular holes 31c, which are formed on the disk portion 31b of the outer control shaft 31, and the plurality of projections 33d, which are formed on the upper wall 33f of the U-D angle knob 33 to be respectively engaged in the plurality of circular holes 31c. Accordingly, the disk portion 31b is fixed to an inner surface (lower surface as viewed in FIG. 14) of the upper wall 33f. With this structure, the boundary between the U-D angle knob 33 and the outer control shaft 31 is not exposed to the outside of the U-D steering device 13UD very much, which makes it easy to wash and clean the U-D steering device 13UD.

In the U-D angle knob 33, the large circular aperture 33b which makes it possible to dismount mold pieces corresponding to the mold pieces 83 through 87 of the L-R angle knob 68 from the inside of the U-D angle knob 33 also makes it possible to dismount and mount the aforementioned assembly of fundamental elements of the locking device for the U-D angle knob 33 from and to the U-D angle knob 33. When the assembly is mounted to the U-D angle knob 33, the large circular aperture 33b is closed in a watertight fashion via the third sealing member group (three annular sealing members) S3 of the assembly of fundamental elements of the locking device for the U-D angle knob 33. Accordingly, the inner space 33i of the U-D angle knob 33 is maintained as a watertight space even though the large aperture 33b is formed on the U-D angle knob 33.

As can be understood from the foregoing, according to the second embodiment of the control device of the endoscope 10, since each of the L-R angle knob 68 and the U-D angle knob 33 is formed as a resin-made hollow member having a single-piece construction, each of the L-R angle knob 68 and the U-D angle knob 33 can be made easily with a low cost of production, and each of the L-R steering device 13LR and the U-D steering device 13UD can be washed and cleaned easily and efficiently.

FIGS. 25 through 28 show the third embodiment of the control device of the endoscope.

Figure 26:
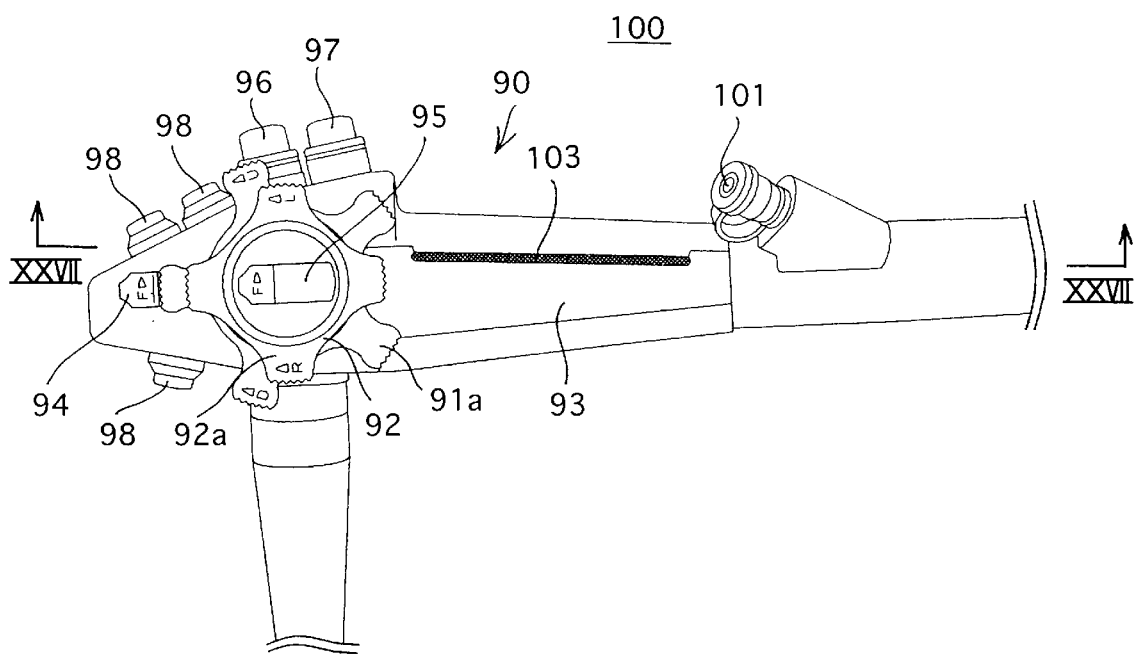
FIG. 26 is a plan view of fundamental part of the endoscope shown in FIG. 24.

The endoscope 100 shown in FIG. 26 is provided with a operational body 90 and an insertion portion (not shown) connected to the operational body 90. The insertion portion is the same as the insertion portion 12 of the first embodiment shown in FIG. 1. The insertion portion extends to the right from the operational body 90 as viewed in FIG. 26. The distal end of the insertion portion is formed as a steerable bendable portion which is to the same as the bendable portion 12a shown in FIG. 1. The operational body 90 is provided with a U-D angle knob (rotational control knob/rotational steering knob) 91 which is manually turned to bend the bendable portion upward and downward, an L-R angle knob (rotational control knob/rotational steering knob) 92 which is manually turned to bend the bendable portion right and left, a U-D lock lever 94 which is manually turned to lock the U-D angle knob 91, and an L-R lock knob 95 which is manually turned to lock the L-R angle knob 92. The operational body 90 is further provided with a grip portion 93.

When the operator uses the endoscope shown in FIG. 26, he/she manually controls the U-D angle knob 91 and the L-R angle knob 92 with his/her fingers (generally, thumb and forefinger) of one hand while holding the grip portion 93 to direct the tip of the steerable bendable portion toward a target part. After the bendable portion is directed to the target part, the operator manually controls the U-D lock lever 94 and the L-R lock knob 95 to lock the U-D angle knob 91 and the L-R angle knob 92 to thereby lock the bendable portion. The operational body 90 is further provided with an air/water suction button 96 for sucking air or water from the tip of the bendable portion, an air/water feeding button 97 for delivering air or water at the tip of the bendable portion, and three endoscope control buttons 98 for remote-controlling an external system such as a video system. The operational body 90 is further provided on the grip portion 93 with a treatment tool insertion opening 101.

Figure 27:
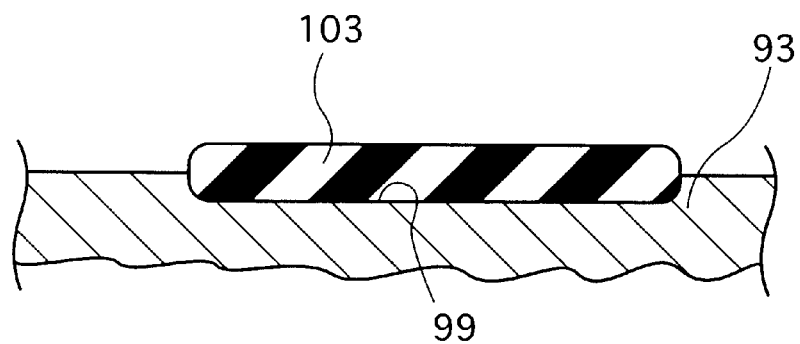
FIG. 27 is a fragmentary cross sectional view of the endoscope, taken along XXVII—XXVII line shown in FIG. 26, viewed in the direction of the appended arrows.

The operational body 90 is further provided on the grip portion 93 with a rubber strip 103 which extends along a longitudinal direction of the grip portion 93. As shown in FIG. 27, the grip portion 93 is provided with an elongated groove 99 in which the rubber strip 103 is fitted. As can be seen in FIG. 27, the rubber strip 103 slightly projects from the external surface of the grip portion 93 to function as a non-slip rubber strip which prevents the operational body 90 from slipping off the hand of the operator.

Figure 25:
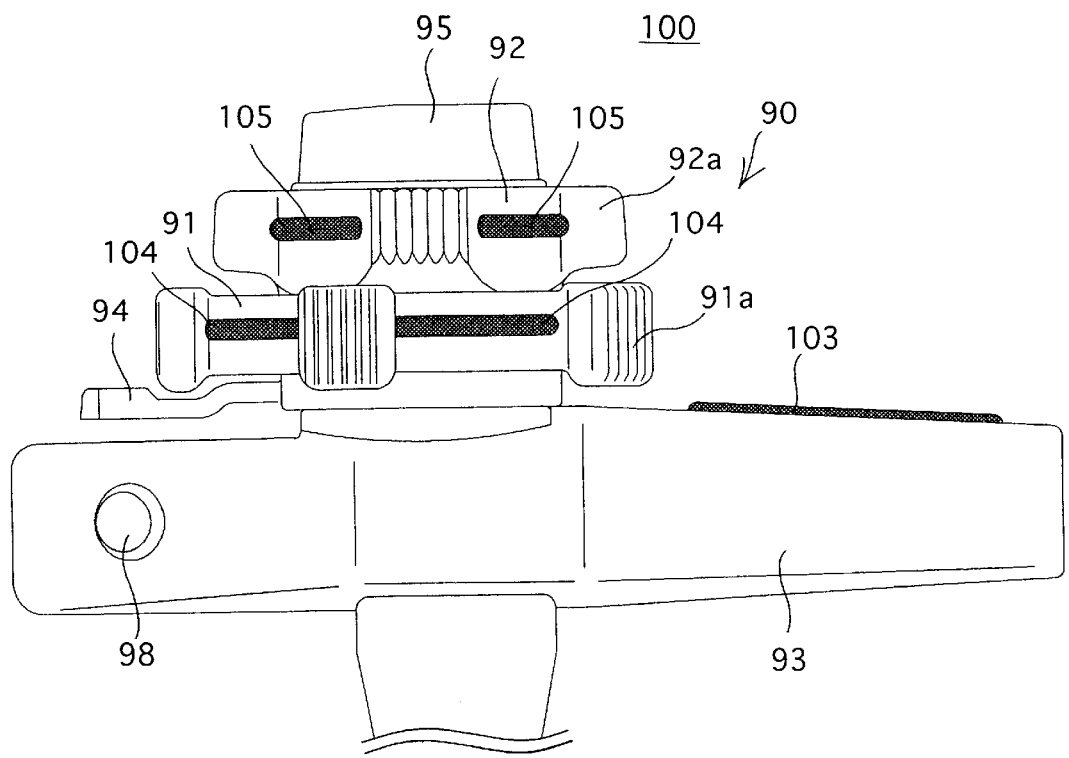
FIG. 25 is a front elevational view of fundamental part of an endoscope having the third embodiment of the control device to which the present invention is applied, showing the outward appearance of the control device.

The U-D angle knob 91 is provided at equi-angular intervals with five projecting portions 91a which extend radially outwards so that the operator can securely hold and turn the U-Dangle knob 91 with his/her fingers engaging with the projecting portions, similar to the U-D angle knob 33 of the first embodiment of the control device of the endoscope 10. The U-D angle knob 91 is provided thereon with five rubber strips 104 (only two of them are shown in FIG. 25) each of which is positioned between corresponding two adjacent projecting portions 91a of the U-D angle knob 91. Namely, the U-D angle knob 91 is provided with five small-diameter portions each of which is positioned between corresponding two adjacent projecting portions 91a of the U-D angle knob 91, while the five rubber strips 104 are fixed to the five small-diameter portions along a circumference of the U-D angle knob 91, respectively. Each rubber strip 104 slightly projects from the external surface of the U-D angle knob 91 in a manner similar to the rubber strip 103.

The L-R angle knob 92 is provided at equi-angular intervals with four projecting portions 92*a* which extend radially outwards so that the operator can securely hold and turn the L-R angle knob 92 with his or her fingers engaging with the projecting portions, similar to the L-R angle knob 23 of the first embodiment of the control device of the endoscope. The L-R angle knob 92 is provided thereon with four rubber strips 105 (only two of them are shown in FIG. 25) each of which is positioned between corresponding two adjacent projecting portions of the L-R angle knob 92. Namely, the L-R angle knob 92 is provided with four small-diameter portions each of which is positioned between corresponding two adjacent projecting portions of the L-R angle knob 92, while the four rubber strips 105 are fixed to the four small-diameter portions along a circumference of the L-R angle knob 92, respectively. Each rubber strip 105 slightly projects from the external surface of the L-R angle knob 92 in a manner similar to the rubber strip 103. Similar to the rubber strip 103 provided on the grip portion 103, each of the rubber strips 104 and 105 functions as a non-slip rubber strip which prevents the fingers of the operator from slipping off the angle knob.

Figure 28:
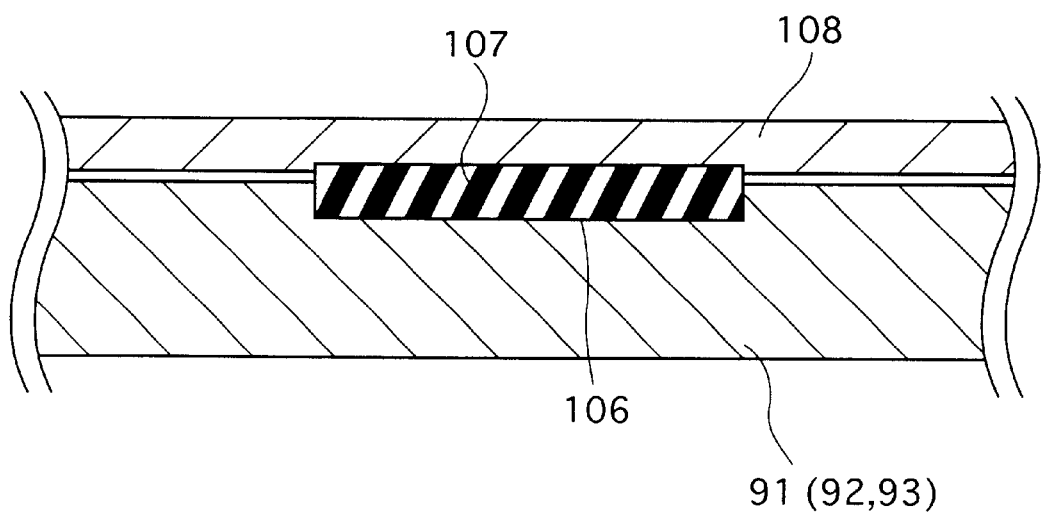
FIG. 28 is a conceptual view for explaining a manner of making a rubber strip which is provided on the operational body of the endoscope shown in FIGS. 25 and 26.

Each of the rubber strips 103, 104 and 105 can be made in such a manner as discussed below. FIG. 28 is a conceptual view for explaining the manner of making each of the rubber strips 103, 104 and 105. Each of the U-D angle knob 91, the L-R angle knob 92 and the grip portion 93, which is made of a synthetic resin or a composite material of a synthetic resin and metal, is provided with a groove 106 in which the corresponding rubber strip 103, 104 or 105 can be fitted. The groove 106 is formed on each of the U-D angle knob 91, the L-R angle knob 92 and the grip portion 93 at the same time each knob is made (e.g., cast). After the knob (91, 92, 93) is made, a strip of rubber material 107 is fitted into the groove 106. Thereafter, the strip of rubber material 107 is vulcanized with a die 108 being placed on the strip of rubber material 107 to form the rubber strip 103, 104 or 105.

The material of each rubber strip 103, 104 and 105 is not limited solely to a particular rubber material, but is preferably a fluororubber (fluorine-contained rubber) or a silicone rubber which is superior in chemical resistance compared to other rubber materials.

Although each of the rubber strips 103, 104 and 105 slightly projects from the external surface of the grip portion 93 or the associated angle knob 91 or 92 in the illustrated embodiment, each of the rubber strips 103, 104 and 105 can be provided so that the external surface thereof is substantially flush with the external surface of the grip portion 93 or the associated angle knob 91 or 92. Although it is preferable that each of the rubber strips 103, 104 and 105 slightly project from the external surface of the grip portion 93 or the associated angle knob 91 or 92 from a viewpoint as to the holding of the endoscope, it is preferable that the external surface of each of the rubber strips 103, 104 and 105 is substantially flush with the external surface of the grip portion 93 or the associated angle knob 91 or 92 from a viewpoint as to cleaning of the endoscope. Accordingly, the amount of projection of each of the rubber strips 103, 104 and 105 can be determined in consideration of these two factors.

Although the strip of rubber material 107 is vulcanized with a die 108 being placed on the strip of rubber material 107 to form the rubber strip 103, 104 or 105, the rubber strip can be made beforehand and fixed to the groove 106 with an adhesive.

Although at least one rubber strip is provided on each of the U-D angle knob 91, the L-R angle knob 92 and the grip portion 93, the fixing positions of the rubber strips are not limited solely to the particular positions described above. For instance, one or more similar rubber strips can be fixed to each of the U-D lock lever 94 and the L-R lock knob 95. Furthermore, the number of rubber strips provided on each of the U-D angle knob 91, the L-R angle knob 92 and the grip portion 93 is not limited solely to the particular number described above.

As can be understood from the foregoing, according to an aspect of the present invention, the inner space of each hollow rotational control knob and the inner space of the operational body of the endoscope have a communicative connection with each other. This structure prevents the internal pressure of the inner space of each hollow rotational control knob from increasing excessively. Therefore, even if a large difference in pressure occurs between the outside and the inside of the endoscope, each hollow rotational control knob is not easily damaged. This makes it possible to reduce the wall thickness of each hollow rotational control knob. Furthermore, in the case where one hollow rotational control knob has an adhesive coated surface, the area of the adhesive coated surface can be made minimal. Accordingly, a control device of an endoscope having lightweight and heavy-duty rotational control knobs is achieved.

Moreover, according to another aspect of the present invention, a control device of an endoscope having hollow rotational steering knobs which can be produced at a low cost of production and which contributes to the maintainability of the endoscope (e.g., which makes it easy to clean the endoscope) is achieved.

Moreover, according to another aspect of the present invention, a control device of an endoscope whose operational body can be securely held, gripped and controlled with little possibility of the operational body slipping off the hand or the fingers of the operator slipping off an rotational control knob during the use of the endoscope.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An endoscope comprising:
   a hollow operational body;
   a hollow shaft provided on said hollow operational body;
   at least one hollow rotational control knob which is rotatably supported on said hollow shaft; and
   an air passage via which an inner space of said hollow operational body and an inner space of said hollow rotational control knob have a communicative connection with each other, wherein said hollow shaft comprises a portion of said passage;
   wherein said hollow rotational control knob is positioned about an axis of said hollow shaft at an intermediate position between opposite ends of said axis, and
   wherein said air passage comprises:
      at least one radial path formed on said hollow shaft to extend in a radial direction of aid hollow shaft to said inner space of said hollow rotational control knob; and
      at least one axial path formed in said hollow shaft so as to have a communicative connection with said radial path, and to extend in a direction of said axis of said hollow shaft to said inner space of said hollow operational body.

2. An endoscope comprising:

a hollow operational body;

a hollow shaft provided on said hollow operational body;

at least one hollow rotational control knob which is rotatably supported on said hollow shaft;

an air passage via which an inner space of said hollow operational body and an inner space of said hollow rotational control knob have a communicative connection with each other, wherein said hollow shaft comprises a portion of said passage; and at least one cylindrical member which is fitted on said hollow shaft, wherein said hollow rotational control knob is positioned about an axis of said hollow shaft at an intermediate position between opposite ends of said axis, and wherein said air passage comprises:

at least one axial path formed in said hollow shaft to extend in a direction of said axis of said hollow shaft to said inner space of said hollow operational body;

at least one first radial path formed on said hollow shaft to extend in a radial direction of said hollow shaft from said axial path to an outer peripheral surface of said hollow shaft;

at least one second radial path formed on said cylindrical member to extend in said direction of said axis of said hollow shaft so as to provide a communicative connection with said axial path and said inner space of said hollow rotational control via said second radial path regardless of a relative rotational position between said cylindrical member and said hollow shaft.

3. The endoscope according to claim 2, wherein said hollow rotational control knob is fixed to said cylindrical member so that said cylindrical member rotates about said hollow shaft together with said hollow rotational control knob when said hollow rotational control knob is turned.

4. The endoscope according to claim 1, wherein said at least one hollow rotational control knob comprises two hollow rotational control knobs which are positioned about said axis of said hollow shaft at different positions between opposite ends of said axis, and wherein said inner space of each of said two hollow rotational control knobs have a communicative connection with said inner space of said hollow operational body via said air passage.

5. The endoscope according to claim 2, wherein said at least one hollow rotational control knob comprises two hollow rotational control knobs which are positioned about said axis of said hollow shaft at different position between opposite ends of said axis, and wherein said inner space of each of said two hollow rotational control knobs have a communicative connection with said inner space of said hollow operational body via said air passage.

6. The endoscope according to claim 1, further comprising another hollow rotational control knob which is positioned at one end of said hollow shaft to be rotatable about said axis of said hollow shaft, wherein an inner space of said another hollow rotational control knob and said inner space of said hollow operational body have a communicative connection with each other via said axial path.

7. The endoscope according to claim 2, further comprising another hollow rotational control knob which is positioned at one end of said hollow shaft to be rotatable about said axis of said hollow shaft, wherein an inner space of said another hollow rotational control knob and said inner space of said hollow operational body have a communicative connection with each other via said at least one axial path.

8. The endoscope according to claim 1, further comprising an insertion portion connected to said hollow operational body, wherein said hollow rotational control knob functions as a manually rotatable control member to bend a steerable distal end of said insertion portion so as to direct a tip of said distal end toward a target.

9. The endoscope according to claim 1, further comprising:

an insertion portion connected to said hollow operational body; and another hollow rotational control knob which is positioned at one end of said hollow shaft to be rotatable about said axis of said hollow shaft;

wherein said hollow rotational control knob functions as a manually rotatable control member to bend a steerable distal end of said insertion portion so as to direct a tip of said distal end toward a target; and wherein said another hollow rotational control knob functions as a manually rotatable lock member to lock said rotational steering knob.

10. An endoscope comprising:

a hollow operational body;

at least one hollow rotational control knob provided on said hollow operational body; and a communicative connection device which provides a communicative connection with an inner space of said hollow operational body and an inner space of said hollow rotational control knob;

wherein said communicative connection device comprises a stationary hollow shaft about which said at least one hollow rotational control knob is turned, at least one radial path provided in said hollow shaft extending in a radial direction of said hollow shaft to the inner space of said at least one hollow rotational control knob, and at least one axial path provided in said hollow shaft and having a communicative connection with the radial path and extending in a direction of the axis of said hollow shaft to the inner space of the hollow operational body.

11. The endoscope according to claim 11, wherein said at least one hollow rotational control knob comprises:

a first angle knob for bending a distal end of an insertion portion of said endoscope in a first direction;

a second angle knob for bending said distal end in a second direction perpendicular to said first direction; and a lock knob, positioned at one end of said hollow shaft, for locking said first knob.

12. An endoscope comprising:

an insertion portion provided at a distal end thereof with a steerable bendable portion; and at least one rotational steering knob which is controlled manually to bend said steerable bendable portion so as to direct a tip of said steerable bendable portion toward a target;

wherein said rotational steering knob is made of a resin material and comprises:

a pair of walls which are separate from each other in a direction of a rotational axis of said rotational steering knob, an aperture being formed on each of said pair of walls; and an outer peripheral wall which extends to connect said pair of walls so as to form said rotational steering knob as a hollow knob;

wherein said pair of walls and said outer peripheral wall comprise a molded single-piece construction.

13. The endoscope according to claim 12, wherein said rotational steering knob is formed by injection molding; and wherein one of said two apertures which are respectively formed on said pair of walls is formed so that at least one mold piece of a mold for injection molding said rotational steering knob can be removed through said one of said two apertures.

14. The endoscope according to claim 12, wherein said outer peripheral wall comprises a plurality of hollow projecting portions which extend radially outwards perpendicularly to said rotational axis.

15. The endoscope according to claim 13, wherein said outer peripheral wall comprises a plurality of hollow projecting portions which extend radially outwards perpendicularly to said rotational axis.

16. The endoscope according to claim 15, wherein said mold comprises:

a first mold piece group for forming an outer surface of said rotational steering knob;

a second mold piece group, positioned in an inner space of said rotational steering knob, for forming inner surfaces of said plurality of hollow projecting portions; and a third mold piece group, positioned in said inner space, for positioning said second mold piece group at a predetermined position in said inner space;

wherein said third mold piece group is taken out of said inner space via said one of said two apertures, subsequently said second mold piece group is moved to a position in said inner space where said second mold piece group can be taken out of said inner space via said one of said two apertures, and subsequently said second mold piece group is taken out of said inner space via said one of said two apertures.

17. The endoscope according to claim 13, further comprising at least one locking device which can be manually operated from an outside of said endoscope to lock said at least one rotational steering knob;

wherein at least one element of said locking device is positioned in said inner space of said at least one rotational steering knob; and wherein said at least one element of said locking device can be dismounted from said inner space via said one of said two apertures.

18. The endoscope according to claim 17, further comprising at least one annular sealing member for sealing a gap between said one of said two apertures and said at least one element of said locking device.

19. The endoscope according to claim 12, further comprising:

a rotational center-shaft about which said at least one rotational steering knob is turned; and at least one control shaft comprising a cylindrical portion rotatably fitted on said rotational center-shaft and a plate portion extending perpendicular to an axis of said rotational center-shaft;

wherein said plate portion is fixed to an inner surface of one of said pair of walls, said inner surface being positioned in an inner space of said at least one rotational steering knob.

20. The endoscope according to claim 19, wherein said inner surface of said one of said two separate walls, to which said plate portion is fixed, comprises:

a plurality of projections, wherein a corresponding plurality of holes are formed on said plate portion;

wherein said plurality of projections are firstly fitted in said corresponding plurality of holes, respectively, and subsequently a tip of each of said plurality of projections is melted by heat to fix said plate portion to said one of said two separate walls.

21. The endoscope according to claim 19, wherein said at least one control shaft is made of metal.

22. An endoscope comprising:

an operational body having an insertion portion extending therefrom;

at least one elongated groove provided in an external surface of a grip portion of said operational body; and non-slip rubber member fixed to an external surface of said operational body, said non-slip rubber member comprising a rubber strip fixed in said at least one elongated groove in the external surface of the grip portion of said operational body, said non-slip rubber strip projecting outwardly from said elongated groove above the external surface of the grip portion of said operational body.

23. The endoscope according to claim 22, wherein said insertion portion comprises a steerable bendable portion; and wherein said operational body comprises at least one rotational steering knob which is turned manually to bend said steerable bendable portion so as to direct a tip thereof toward a target, said at least one non-slip rubber member being fixed to an external surface of said at least one rotational steering knob.

24. The endoscope according to claim 22, wherein said at least one non-slip rubber member is made of a fluorine-contained rubber.

25. The endoscope according to claim 22, wherein said at least one non-slip rubber member is made of silicone rubber.

26. The endoscope according to claim 22, wherein said at least one non-slip rubber member is made of a rubber which has an outstanding performance in chemical resistance.

* * * * *